United States Patent [19]

Radel et al.

[11] 4,342,314

[45] Aug. 3, 1982

[54] RESILIENT PLASTIC WEB EXHIBITING FIBER-LIKE PROPERTIES

[75] Inventors: Clifford J. Radel, Cheviot; Hugh A. Thompson, Fairfield, both of Ohio

[73] Assignee: The Procter & Gamble Company, Cincinnati, Ohio

[21] Appl. No.: 206,410

[22] Filed: Nov. 13, 1980

Related U.S. Application Data

[63] Continuation-in-part of Ser. No. 17,506, Mar. 5, 1979, abandoned.

[51] Int. Cl.³ .............................................. A61F 13/16
[52] U.S. Cl. .................................. 128/287; 428/131; 428/138; 428/156; 428/913
[58] Field of Search ............... 428/131, 133, 138, 155, 428/156, 72, 73, 178, 297, 298, 299, 913, 137, 288; 128/155, 156, 284, 285, 287, 296, 290 R, 290 W

[56] References Cited

U.S. PATENT DOCUMENTS

| | | | |
|---|---|---|---|
| Re. 23,910 | 12/1954 | Smith et al. | |
| Re. 29,524 | 1/1978 | Spencer | |
| 691,804 | 1/1902 | Parker | 428/131 |
| 2,166,366 | 7/1939 | Norris | 156/626 |
| 2,776,451 | 1/1957 | Chavannes | 264/500 |
| 2,809,392 | 10/1957 | Armstrong | |
| 2,816,025 | 12/1957 | Dahlberg | 29/115 |
| 2,820,985 | 1/1958 | Cresswell | |
| 2,857,657 | 10/1958 | Wheeler | 29/163.5 R |
| 2,926,490 | 3/1960 | Eaton et al. | |
| 3,054,148 | 9/1962 | Zimmerli | |
| 3,123,446 | 3/1964 | Wheeler | 428/593 |
| 3,174,837 | 3/1965 | Mears | |
| 3,312,583 | 4/1967 | Rochlis | 428/88 |
| 3,390,447 | 7/1968 | Mears | |
| 3,485,705 | 12/1969 | Harmon | 428/113 |
| 3,560,601 | 2/1971 | Johnson et al. | 264/504 |
| 3,674,221 | 7/1972 | Rumersmo | |
| 3,703,897 | 11/1972 | Mack et al. | 128/156 |
| 3,814,101 | 6/1974 | Kozak | 128/287 |
| 3,844,027 | 10/1974 | Hagan et al. | 228/209 |
| 3,929,135 | 12/1975 | Thompson | 128/287 |
| 3,952,745 | 4/1976 | Duncan | |
| 3,957,414 | 5/1976 | Bussey | 424/384 |
| 3,967,623 | 7/1976 | Butterworth et al. | 128/287 |
| 3,979,494 | 9/1976 | Ericson | 260/951 |
| 3,989,867 | 11/1976 | Sisson | 428/132 |
| 4,038,040 | 7/1977 | Nagl | 428/596 |
| 4,041,951 | 8/1977 | Sanford | 128/287 |
| 4,077,410 | 3/1978 | Butterworth et al. | 128/287 |
| 4,133,310 | 1/1979 | Lloyd et al. | 128/156 |
| 4,151,240 | 4/1979 | Lucas et al. | |
| 4,276,338 | 6/1981 | Ludwa et al. | 428/137 |

FOREIGN PATENT DOCUMENTS 2014508  8/1979  United Kingdom .
2014903  9/1979  United Kingdom .

*Primary Examiner*—James J. Bell
*Attorney, Agent, or Firm*—E. Kelly Linman; John V. Gorman; Richard C. Witte

[57] ABSTRACT

A resilient plastic web exhibiting a fiber-like appearance and tactile impression and method and apparatus for its manufacture. In a preferred embodiment, the web exhibits a three-dimensional microstructure comprising a regulated continuum of debossed areas of non-uniform cross-section along their length. In a particularly preferred embodiment, the debossed areas comprise capillary networks interconnecting the first and second surfaces of the web, said networks being of decreasing size in the direction of said second surface to promote fluid transport from the first surface of the web to the second surface and inhibit the flow of fluid in the reverse direction. Forming surfaces utilized to produce said webs are constructed by laminating a multiplicity of thin plates having patterns of apertures therein to form an integral structure exhibiting properties and characteristics unachievable by prior art machining and weaving techniques. In a particularly preferred embodiment, the individual lamina from which the laminate forming structure is comprised are produced utilizing photoetching techniques, thus making it feasible to produce nearly any desired level of intricacy in the resultant laminate structure. Preferred means for interconnecting said laminate structures with one another without disrupting the three-dimensional pattern in the area of joinder are also disclosed.

37 Claims, 16 Drawing Figures

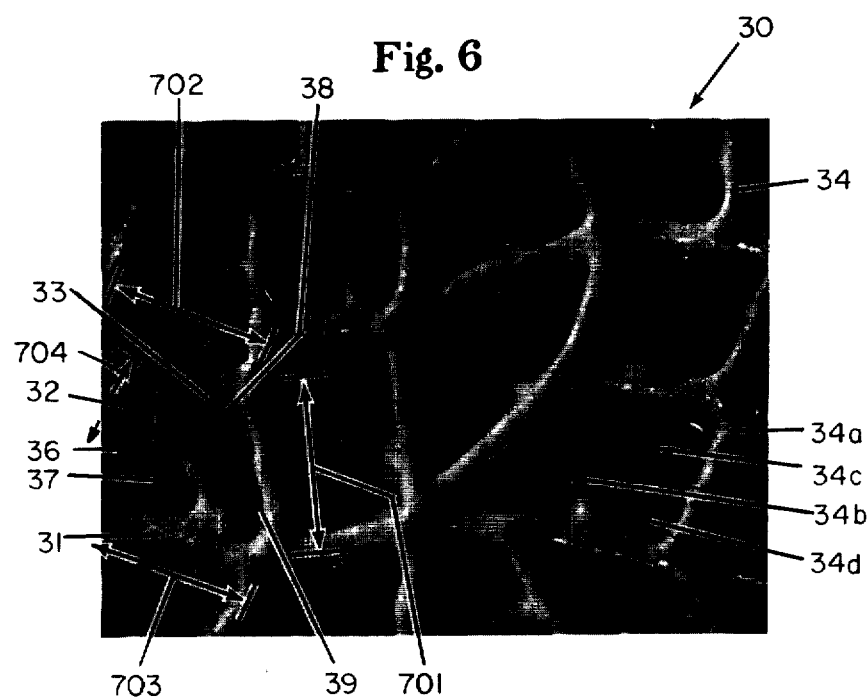

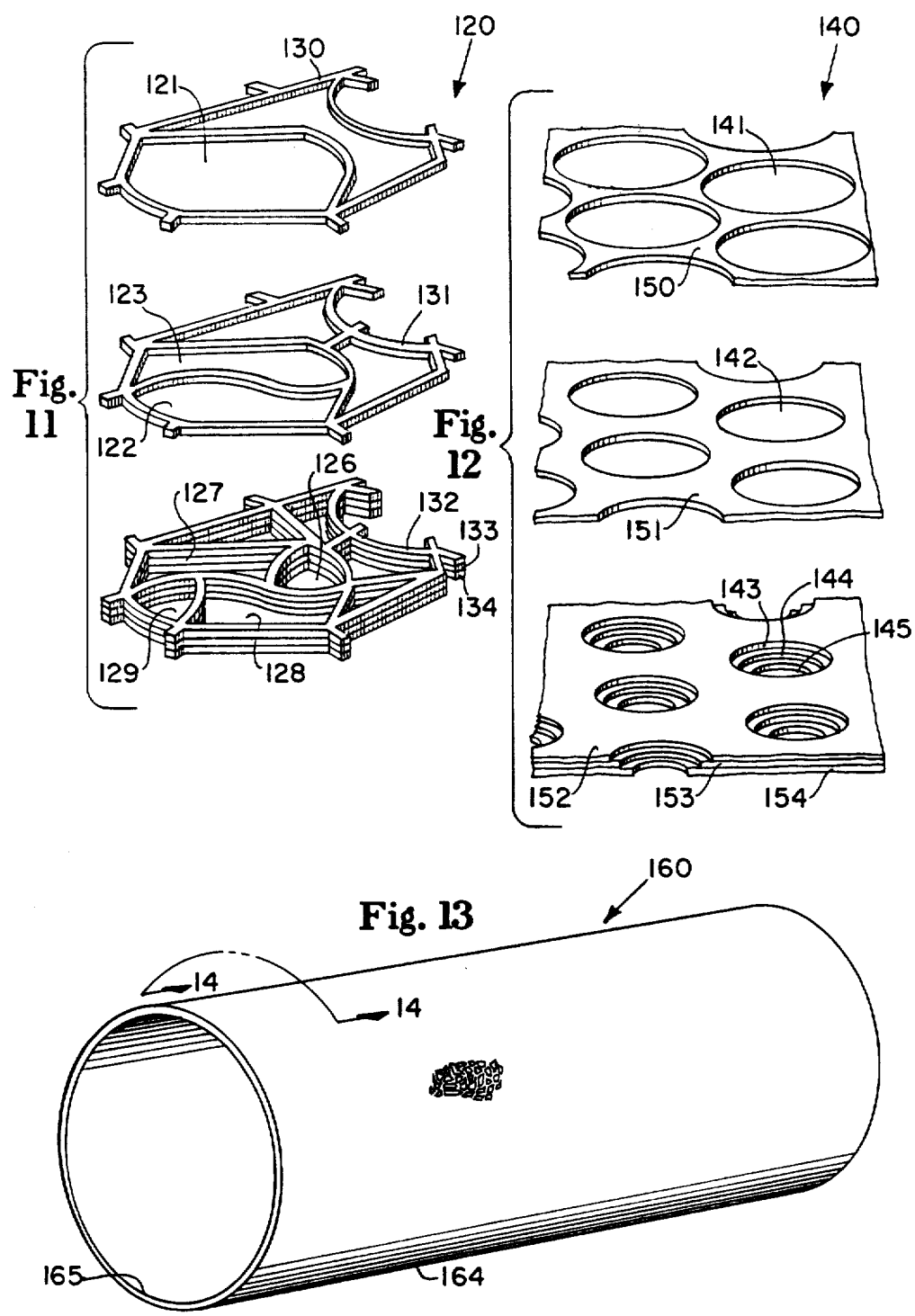

RESILIENT PLASTIC WEB EXHIBITING FIBER-LIKE PROPERTIES

CROSS-REFERENCE TO RELATED APPLICATION

This application is a continuation-in-part of co-pending application Ser. No. 17,506 filed Mar. 5, 1979 in the name of the present applicants, and now abandoned.

TECHNICAL FIELD

The present invention has relation to resilient plastic webs exhibiting many of the three-dimensional, fiber-like properties and characteristics previously obtainable only in fibrous webs.

The present invention has further relation to resilient fluid-pervious plastic webs which exhibit a combination of desirable, but previously incompatible attributes of prior art fibrous webs and prior art plastic webs in a single structure without deleterious side effects.

The present invention has further relation to the provision of method and apparatus for forming plastic webs exhibiting the aforementioned attributes.

BACKGROUND ART

It has long been known in the disposable absorbent bandage art that it is extremely desirable to construct absorptive devices, such as disposable diapers, sanitary napkins, and the like, presenting a dry surface feel to the user to improve wearing comfort and to minimize the development of undesirable skin conditions due to prolonged exposure to moisture absorbed within the bandage. One viable prior art solution to the aforementioned problem is disclosed in U.S. Pat. No. 4,041,951 issued to Sanford on Aug. 16, 1977 and hereby incorporated herein by reference. The Sanford patent discloses a preferred disposable diaper structure comprising a substantially planar, moisture absorbent layer disposed between a soft topsheet and a moisture-resistant backing sheet. The nonwoven fibrous topsheet preferably comprises an integral structure containing a multiplicity of depressed areas which intimately contact the uppermost surface of a substantially planar, moisture absorbent layer. The nondepressed areas of the topsheet contact the wearer's skin in-use. In a particularly preferred embodiment, the nonwoven fibrous topsheet is comprised of a substantially hydrophobic material exhibiting wet resilience such that the topsheet tends to resume its substantially three-dimensional character upon removal of pressure applied against the topsheet by the body movements of the wearer. The nondepressed areas of the topsheet, which are of substantially the same density as the depressed areas, tend to isolate the wearer's skin from moisture contained within the moisture absorbent layer, thereby providing surface dryness and resistance to rewetting when the structure is temporarily subjected to pressure resulting from the wearer's body movements.

U.S. Pat. No. 3,814,101 issued to Kozak on June 4, 1974, attacks the problem of a wet topsheet in a manner slightly different from the use of hydrophobic nonwoven materials. Kozak suggests a topsheet of a nonfibrous, hydrophobic film which is provided with a plurality of valvular slits which restrict the reverse flow of liquid from the absorbent element of the device.

U.S. Pat. No. 3,929,135 issued to Thompson on Dec. 30, 1975, and hereby incorporated herein by reference, suggests a topsheet comprised of liquid-impermeable material, but provided with tapered capillaries, said capillaries having a base opening in the plane of the topsheet and an apex opening remote from the plane of the topsheet, said apex opening being in intimate contact with the absorbent pad utilized in the disposable absorbent bandage. The topsheet disclosed in the Thompson patent allows the free transfer of fluids from the body into the absorbent element of the device while inhibiting the reverse flow of these fluids, thereby providing a relatively much drier surface in contact with the user than had been previously obtainable. However, contrary to expectations, it has been learned that despite the highly effective fluid transfer and fluid isolation characteristics exhibited by plastic topsheets of the type generally disclosed in the Thompson patent and their proven compatibility with the wearer's skin, many users find it psychologically undesirable to employ a material which is perceivably plastic in contact with their skin. It is believed that this user reaction is due partly to the highly regulated tapered capillary pattern on the wearer-contacting surface of the topsheet and partly to the glossy appearance of the film. Users are prone to view both of these characteristics negatively when dealing with plastic films which will contact the user's skin.

Prior art method and apparatus for embossing, vacuum forming and/or perforating plastic film have substantially precluded the elimination of such plastic characteristics exhibited by formed films. U.S. Pat. No. 2,809,392 issued to Armstrong on Oct. 15, 1957 discloses a prior art vacuum forming drum utilized to emboss a heat softened thermoplastic film drawn across its surface. The vacuum drum comprises a rolled hollow shell provided with a plurality of circumferential grooves which are positioned progressively closer together toward the ends of the drum. Holes about 1/16 inch in diameter are drilled through the shell at circumferentially spaced points in the grooves. The heat softened film is embossed by the application of vacuum to the interior surfaces of the drum while the film is in contact with the peripery thereof. As should be clear from the foregoing, the pattern of emboss is inherently governed by machining limitations utilized in constructing the drum.

U.S. Pat. Re. No. 23,910 issued to Smith et al. on Dec. 14, 1954 discloses yet another prior art method and apparatus for producing textured plastic films. The Smith et al. patent suggests the use of a suction box located beneath the surface of a woven wire mesh to draw a heat softened plastic film into conformity with the woven wire mesh. The patent further suggests that a specially patterned belt or fabric could be employed to deform the film in its own likeness by supporting the belt or fabric on the woven wire mesh. In yet another embodiment, the process is carried out utilizing the cylindrical surface of a drum. Nonetheless, the patterns which can be imparted to the film are governed by weaving limitations in the case of the woven wire and fabric and machining/punching limitations in the case of the patterned belt or drum. Furthermore, it is preferred, according to the teachings of Smith et al., that the forming belt and the forming drum be utilized to produce discrete lengths of film rather than continuous webs in order to avoid creating joint marks where the ends of the belt or the ends of the drum are joined together.

U.S. Pat. No. 3,054,148 issued to Zimmerli on Sept. 18, 1962 discloses a process for producing a perforated plastic sheet. The process comprises subjecting a plasticized plastic sheet or film to the action of pressure over a perforated support or molding element. The softened plastic material is caused to flow into the perforations of the molding element to a depth which can be regulated by control of such factors as the degree of softness of the material, the direction of pressure flow and the relative thickness of the plastic sheet. The molding element preferably comprises a drum which may be made from a metal sheet having the perforated design stamped or otherwise cut from the sheet. However, in the production of simulated fabrics or woven materials, the molding element preferably comprises a woven wire mesh.

A particularly preferred method for continuously debossing and, if desired, perforating a plastic film is disclosed in the commonly assigned co-pending patent application of Malcolm B. Lucas and Robert H. Van Coney entitled "METHOD OF AND APPARATUS FOR DEBOSSING AND PERFORATING A RUNNING RIBBON OF THERMOPLASTIC FILM", U.S. Ser. No. 733,961, filed Oct. 19, 1976, issued on Apr. 24, 1979 as U.S. Pat. No. 4,151,240, and hereby incorporated herein by reference. The Lucas et al. application which, in a preferred embodiment, discloses means for forming a plastic film exhibiting a regulated pattern of tapered capillaries as generally disclosed in the aforementioned patent to Thompson, causes a ribbon of planar thermoplastic film to be forwarded from a supply roll, thence about a circumferentially extending portion of a rotating debossing/perforating cylinder and then downstream where the debossed and perforated film may be further processed or wound on a spool to form a roll. The debossing/perforating cylinder preferably comprises a perforated tubular member through which a plurality of independently adjustable levels of vacuum can be applied from within the cylinder to circumferentially spaced sections of the film in contact with the exterior surface of the perforated tubular member. The apparatus further causes a virtual curtain of hot air to be directed radially inwardly towards a predetermined zone of the perforated tubular member. Thus, vacuum applied from within the cylinder acts in concert with the curtain of hot air which flash heats the film sufficiently to effect debossing and perforating of the film running circumferentially about the rotating cylinder. The apparatus may further control tension in the film both upstream and downstream of the debossing cylinder at predetermined constant levels. The disclosed method for making the perforated tubular forming member preferably entails forming the member inside out by electrodepositing nickel about the exterior surfaces of a pattern cylinder having outwardly extending conical projections located about its periphery, and then turning it right side out by slitting it longitudinally, reverse rolling it into the desired tubular shape, and seaming it along the edges thus formed. From the foregoing it is clear that, even in this preferred film forming process, the particular shape or pattern imparted to the thermoplastic film on the surface of the forming cylinder is indirectly governed by limitations inherent in the machining or metal displacing processes utilized to form the pattern cylinder.

Accordingly, it is an object of the present invention to provide a plastic web exhibiting a three-dimensional pattern of embossments and/or perforations or any desired combination thereof which is independent of the machining and weaving limitations inherent in prior art forming surfaces.

It is another object of the present invention to provide a forming surface exhibiting nearly any desired three-dimensional structure at a scale so fine that the resultant plastic sheets formed thereon exhibit fiber-like properties and characteristics.

It is another object of the present invention to provide a continuous, three-dimensionally patterned forming surface, the ends of which may, if desired, be secured to one another substantially without disruption to the three-dimensional pattern contained therein.

It is yet another object of the present invention to provide a forming surface exhibiting a degree of surface roughness or texture to further aid in reducing the glossy appearance typically exhibited by plastic films.

It is still another object of the present invention to provide a fluid-pervious plastic web exhibiting a fiber-like appearance and tactile impression, i.e., an overall impression of softness, said web further exhibiting a fine scale three-dimensional microstructure comprising a regulated continuum of capillary networks, preferably of steadily decreasing size, originating in and extending from one surface of said film and terminating in the form of apertures in the opposite surface thereof to promote rapid liquid transport in the direction of decreasing capillary size. As utilized herein, the term "microstructure" refers to a structure of such fine scale that its precise detail is readily perceived by the human eye only upon magnification by microscopic or other means well known in the art. The term "fiber-like", as utilized herein to describe the appearance of plastic webs of the present invention, refers generally to any fine scale pattern of debossments or apertures, random or non-random, reticulated or non-reticulated, which connotes an overall appearance and impression of a woven or non-woven fibrous web when viewed by the human eye.

DISCLOSURE OF INVENTION

The present invention pertains, in a preferred embodiment, to the provision of resilient plastic webs exhibiting a combination of fiber-like and plastic properties previously unachievable utilizing known prior art methods and apparatus for their manufacture. In a preferred embodiment, it provides a fluid-pervious plastic web having first and second surfaces, at least one and preferably both of said surfaces exhibiting a fiber-like appearance and tactile impression. In a particularly preferred embodiment, said web exhibits a fine scale three-dimensional microstructure comprising a regulated continuum of capillary networks of steadily decreasing size originating in and extending from a first surface of the web and terminating in the form of apertures in a second surface thereof to promote rapid fluid transport from said first surface to said second surface. Resilient plastic webs of the present invention have widespread application, particularly in absorbent structures such as bandages, diapers, and catamenial appliances such as sanitary napkins, tampons, and the like. Said webs, when made fluid-pervious, are particularly well suited for use as a wearer-contacting topsheet in such absorbent structures. However, the present invention is in no way limited to use as a topsheet in such absorbent structures. Its use may readily be extended to great advantage in many applications as an improved replacement for prior art fibrous webs and/or prior art plastic webs where a particular combination of previously unachievable properties or characteristics is desired in a single structure. Furthermore, plastic webs of the present invention may be used in lieu of prior art plastic webs to produce a superior end product. For example, a fiber-like plastic web of the present invention could serve as a breathable backsheet resistant to aqueous liquid passage as generally taught by U.S. Pat. No. 3,989,867 issued to Sisson on Nov. 2, 1976 and hereby incorporated herein by reference. This would require orienting the web so as to place the surface exhibiting the finer scale capillary openings in contact with the absorbent pad and the surface exhibiting the larger scale capillary openings opposite the wearer-contacting surface of the absorbent structure.

Forming surfaces of the present invention are preferably constructed by stacking a multiplicity of thin metal sheets or laminae upon one another to form a three-dimensional continuum exhibiting the particular structural features desired for the application of interest and bonding said stack of sheets to one another at contact points to form an integral laminate structure without destroying said continuum. In the simplest embodiment of the present invention, the thin metal sheets exhibit identical patterns of apertures, and are stacked so that the apertures in each sheet coincide with one another. However, in a particularly preferred embodiment, at least a portion of said sheets exhibit either dissimilar patterns of apertures or similar patterns of apertures of differing size. While said laminate structure may, of course, be utilized as a forming surface while in a planar condition, it is preferably further processed by causing the uppermost surface of said laminate structure to assume a radius of curvature greater than that of the lowermost surface of said laminate structure without causing delamination, thereby causing said laminate structure to assume a substantially tubular shape, and securing the opposing free edges of said laminate structure to one another without creating a discontinuity in either the exterior surface or the three-dimensional continuum existing throughout the tubular member thus formed. In a particularly preferred embodiment of the present invention, the free edges of the tubular laminate structure are secured to one another by lap seaming to substantially avoid any discontinuity in the three-dimensional pattern exhibited at any point along its surface.

The laminate tubular member, which permits continuous web processing, is preferably utilized in a vacuum forming operation which is conducted in concert with a curtain of hot air which flash heats the plastic film sufficiently to effect substantial conformance to the three-dimensional pattern embodied in the tubular member. In other embodiments, the film may be preheated prior to contact with the forming surface, or the plastic material may be direct cast from an extruder die onto the forming surface. In any event, the film is preferably cooled while in contact with the tubular forming member and thereafter removed.

As will be apparent from the description contained herein, the present invention may be practiced to great advantage to produce films exhibiting continuous regulated patterns, continuous random patterns, or interrupted patterns merely by constructing the tubular forming member with the desired pattern on its periphery. Furthermore, the film processed thereon may be debossed and perforated, debossed only, perforated only, or any desired combination thereof.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 6 is a plan view photograph enlarged approximately 27 times of a preferred fiber-like plastic web of the present invention, said fiber-like web having a three-dimensional microstructure comprising a regulated continuum of capillary networks of steadily decreasing size extending from its uppermost to its lowermost surface;

FIG. 11 is an enlarged, partially exploded, perspective view of a photoetched laminate structure of the type generally illustrated in FIG. 8, the laminae in the uppermost portions of said structure being exploded for clarity to illustrate the manner in which the opening patterns in each lamina are superposed upon one another to produce a unique three-dimensional continuum of capillary networks of steadily decreasing size extending from the uppermost to the lowermost surface of the laminate;

FIG. 12 is a perspective view similar to FIG. 11 of an alternate pattern comprised of uniformly spaced holes of steadily decreasing diameter, said pattern being particularly suited to formation of a prior art plastic web having a pattern of the type generally illustrated in FIGS. 4 and 5;

FIG. 13 is a perspective view of a tubular member formed by rolling a planar laminate structure of the type generally illustrated in FIG. 8 to the desired radius of curvature and joining the free ends thereof to one another;

DETAILED DESCRIPTION OF THE PRESENT INVENTION

While the present invention will be described in the context of providing a fiber-like, resilient plastic web suitable for use as a topsheet on an absorbent bandage such as a disposable diaper, the present invention is in no way limited to such application. To the contrary, the present invention may be practiced to great advantage in many situations where it is desired to produce a plastic film or web exhibiting either a perforate or an imperforate three-dimensional structure having properties, characteristics, aesthetics, fineness of detail, etc., not previously obtainable due to machining and/or weaving limitations inherent in prior art processes for producing suitable film forming surfaces. The patterns created may be of any desired shape, they may be regulated or random, reticulated or non-reticulated, continuous or interrupted, perforated or unperforated or any desired combination thereof. The detailed description of a preferred structure and its use as a topsheet in a disposable diaper will allow one skilled in the art to readily adapt the invention to other devices.

Figure 1:
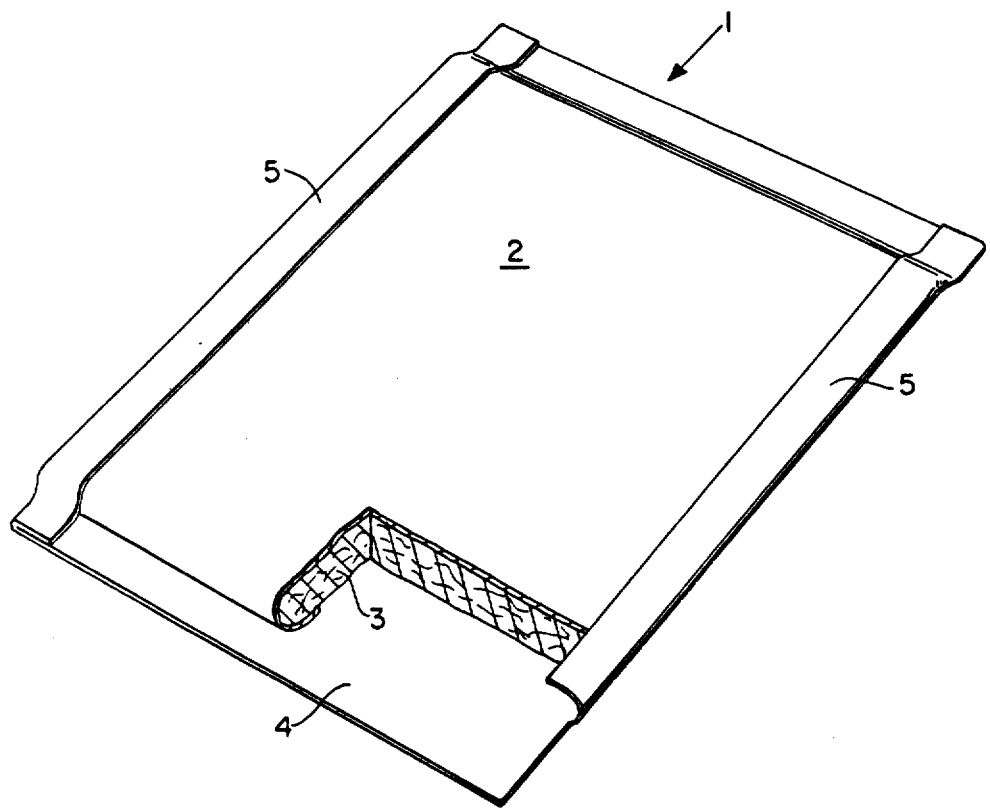
FIG. 1 is a simplified perspective representation of an unfolded disposable diaper with portions of its components cut away.

FIG. 1 is a perspective view of a diaposable diaper in an unfolded condition. Various layers have been cut away to more clearly show the structural details of this embodiment. The disposable diaper is referred to generally by the reference numeral 1. The fluid-pervious topsheet is shown at 2. The other two major components of the disposable diaper 1 are the absorbent element or pad 3 and the fluid-impervious backsheet 4. In general, the side flaps 5 of the backsheet 4 are folded so as to cover the edges of the absorbent pad 3 and topsheet 2. Topsheet 2 is generally folded to completely enclose the ends of the absorbent pad 3. The drawing of diaper 1 in FIG. 1 is a simplified representation of a disposable diaper. A more detailed description of a preferred embodiment of a disposable diaper is contained in U.S. Pat. No. 3,952,745 issued to Duncan on Apr. 27, 1976, said patent being hereby incorporated herein by reference.

Figure 2:
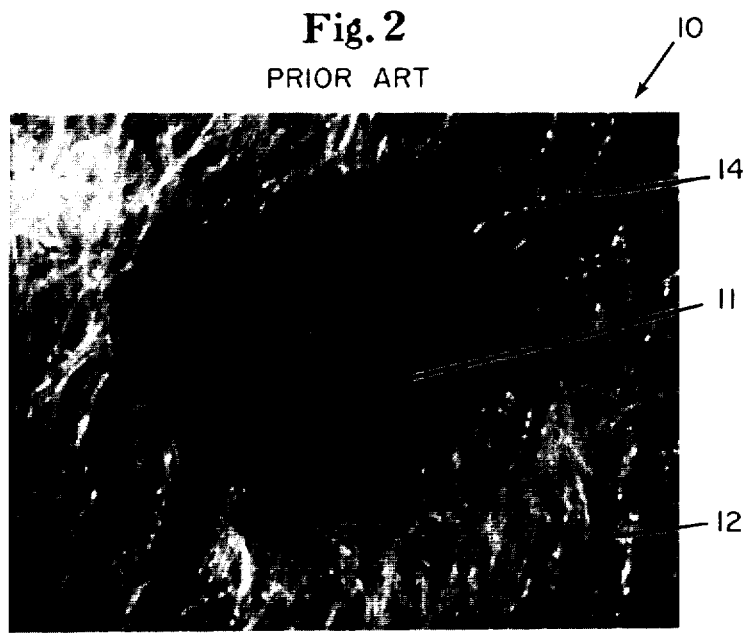
FIG. 2 is a plan view photograph enlarged approximately 27 times of a prior art nonwoven fibrous topsheet of the type generally disclosed in U.S. Pat. No. 4,041,951, as viewed from the wearer-contacting surface thereof.

FIG. 2 is a plan view photograph enlarged approximately 27 times of the wearer-contacting surface 14 of a prior art nonwoven, generally hydrophobic fibrous web 10 which has been found suitable for use as a topsheet 2 in disposable diaper 1. The web 10 preferably comprises an integral three-dimensional structure containing a multiplicity of depressed areas 11 which intimately contact the uppermost surface of the moisture absorbent pad 3, while the nondepressed areas 12 contact the wearer's skin in-use. Due to the wet resilience and increased overall caliper of the nonwoven fibrous web 10, the nondepressed areas 12, which are of substantially the same density as the depressed areas 11, tend to isolate the wearer's skin from moisture contained within the moisture absorbent pad 3, thereby providing improved surface dryness and improved resistance to rewetting when the structure is temporarily subjected to pressure resulting from the wearer's body movements.

The prior art nonwoven fibrous web 10 shown in FIG. 2 is generally in accordance with the teachings of U.S. Pat. No. 4,041,951 issued to Sanford on Aug. 16, 1977 and incorporated herein by reference. An object achieved by the Sanford invention is the provision of a three-dimensional topsheet which permits the free transfer of fluids discharged from the wearer's body into the absorbent element of the absorptive device and thereafter tends to isolate the wearer's skin from the fluids absorbed within the absorbent element. A further object achieved by the Sanford invention is the provision of a nonwoven fibrous topsheet which presents the user with a soft and dry nonirritating surface in contact with the skin.

Figure 3:
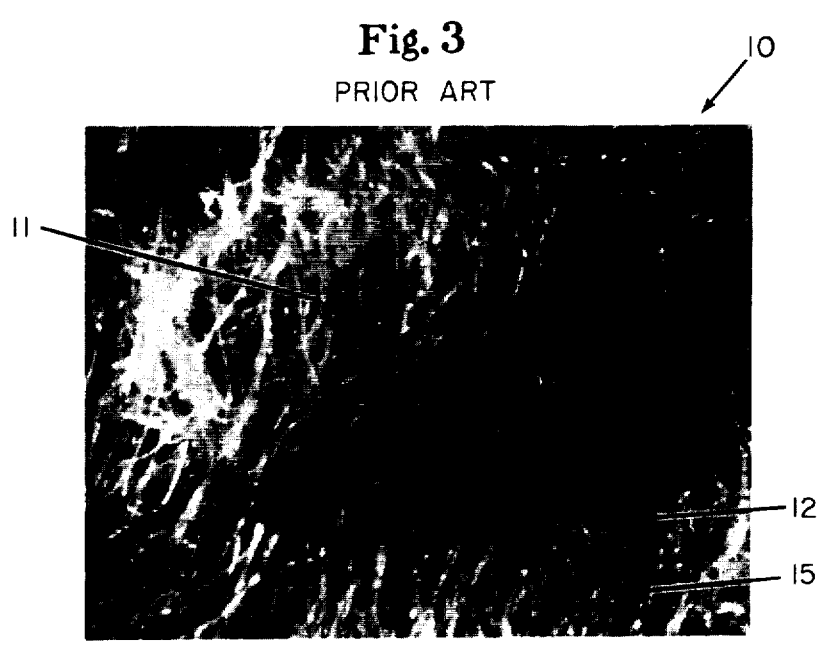
FIG. 3 is a plan view photograph enlarged approximately 27 times of the nonwoven fibrous topsheet shown in FIG. 2, but taken from the absorbent pad contacting surface of the topsheet.

FIG. 3 is a plan view photograph enlarged approximately 27 times of the nonwoven fibrous web 10 illustrated in FIG. 2, but taken from the lowermost or absorbent element-contacting surface 15 of the material.

Figure 4:
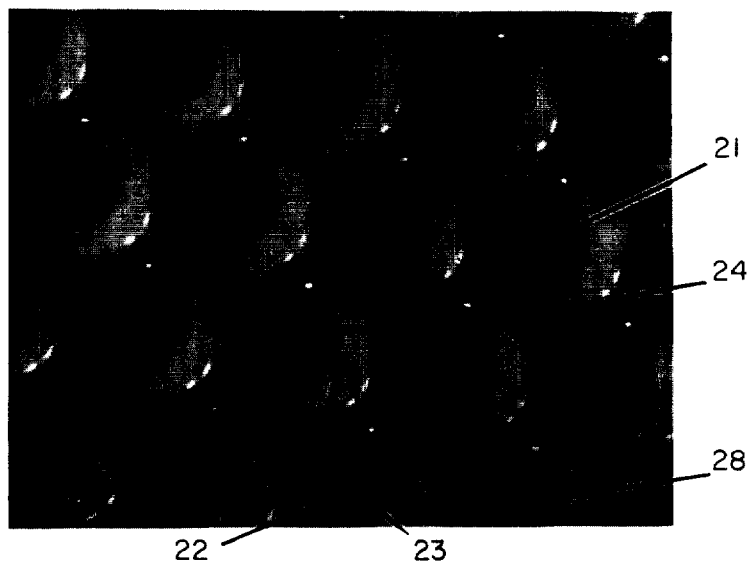
FIG. 4 is a plan view photograph enlarged approximately 27 times of a prior art vacuum formed plastic web of the type generally disclosed in U.S. Pat. No. 3,929,135, said photograph being taken from the wearer-contacting surface of the web.

FIG. 4 is a plan view photograph enlarged approximately 27 times of the wearer-contacting surface 24 of a prior art three-dimensional, fluid-pervious plastic web or film which has also been found particularly suitable as a topsheet 2 for disposable diaper 1. The fluid pervious plastic web 20 illustrated in FIG. 4 exhibits a multiplicity of tapered capillaries 21 of critical diameters and tapers, each capillary having a base opening 22 in the wearer-contacting plane 28 of the web and an apex opening 23 remote from the wearer-contacting plane of the web. The fluid-pervious plastic web 20, which was vacuum formed from 2.5 mil thick unembossed polyethylene, is generally in accordance with the teachings of U.S. Pat. No. 3,929,135 issued to Thompson on Dec. 30, 1975 and incorporated herein by reference. The tapered capillaries 21 contained in thermoplastic web 20 of FIG. 4 have a base opening 22 measuring approximately 0.040 inches, an apex opening 23 measuring approximately 0.016 inches, an overall height of approximately 0.012 inches and a density of approximately 625 evenly spaced apertures per square inch. The tapered capillaries 21 allow the free transfer of fluids from the wearer's body into the absorbent element 3 of the diaper 1 illustrated in FIG. 1 while inhibiting reverse flow of the absorbed fluids, thereby providing a relatively dry surface in contact with the wearer.

Despite the effective functioning of the prior art fluid-pervious plastic web 20 in topsheet applications for disposable absorbent bandages, it has been observed that users often psychologically resist placing a plastic material in contact with the skin. It is believed that this is due in large part to the extremely regulated nature of the pattern of capillaries 21 in the prior art plastic web 20, and also to the slickness or gloss which the user perceives in merely looking at any prior art plastic web or film. This slickness phenomenon is further illustrated in FIG. 5 which is a photographic reproduction enlarged approximately 27 times of the lowermost or absorbent element-contacting surface 25 of the plastic web 20 shown in FIG. 4.

In FIG. 6 is shown a plan view photograph enlarged approximately 27 times actual size of a preferred embodiment of a three-dimensional, fiber-like, fluid-pervious plastic web 30 of the present invention. As can be seen in the enlarged photograph of FIG. 6, the web's fiber-like appearance is comprised of a continuum of fiber-like elements, each end of said fiber-like elements being interconnected to at least one other of said fiber-like elements. In the embodiment disclosed in FIG. 6, the interconnected fiber-like elements are substantially non-aligned with respect to one another. The fiber-like plastic web 30 is particularly well suited for use as a diaper topsheet 2 in a disposable diaper 1 of the type generally illustrated in FIG. 1. FIG. 6 is an illustration of the wearer-contacting or uppermost surface 34 of the web 30. The web 30, which exhibits a fiber-like appearance, embodies a three-dimensional microstructure comprising a regulated continuum of capillary networks of steadily decreasing size extending from the uppermost or wearer-contacting surface 34 to the lowermost or absorbent pad-contacting surface 35 thereof to promote rapid liquid transport from the uppermost to the lowermost surface of the web without lateral transmission of said liquid between adjacent capillary networks.

Figure 6A:
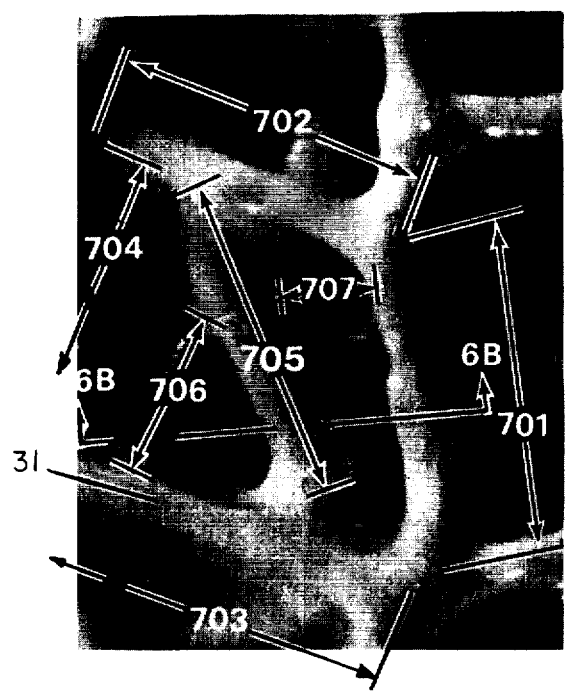
FIG. 6A is a further enlarged plan view photograph of one of the capillary networks illustrated in FIG. 6.

A typical capillary network of the type generally shown in FIGS. 6 and 6A comprises an uppermost capillary opening 31 formed by a multiplicity of primary fiber-like elements, i.e., elements 701, 702, 703 and 704 (not completely shown), interconnected to one another in uppermost plane 34a of the web 30, said opening being further subdivided into smaller capillary openings 32 and 33 by secondary fiber-like element 705 at an intermediate plane 34b. Capillary openings 32 and 33 are further subdivided by tertiary fiber-like elements 706 and 707 into even smaller capillary openings 36, 37 and 38, 39, respectively, at plane 34c of the thermoplastic web 30.

Figure 6B:
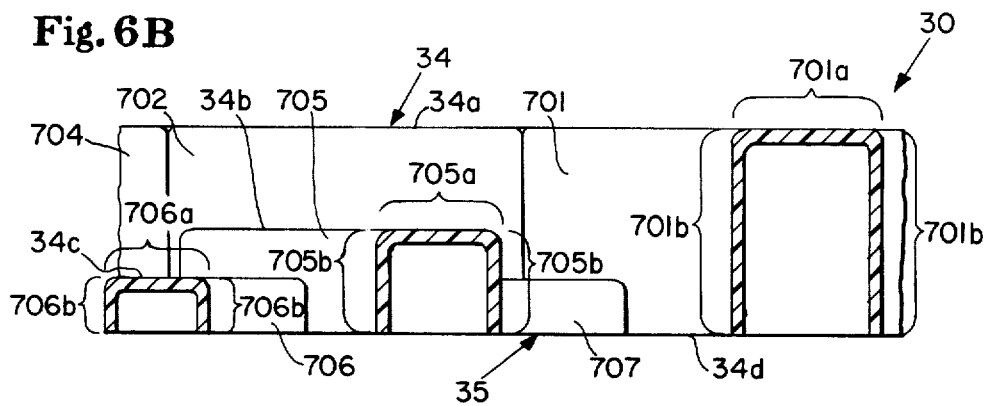
FIG. 6B is an enlarged cross-sectional illustration of a web of the type generally shown in FIG. 6 taken along section line 6B—6B in FIG. 6A.

As can be seen from FIG. 6B, which is taken along section line 6B—6B of FIG. 6A, planes 34b and 34c are generally parallel to and located intermediate planes 34a and 34d. The resilient three-dimensional web 30 shown in FIG. 6 has a first wearer-contacting surface 34 located in plane 34a and a second adsorbent pad-contacting surface 35 located in plane 34d. As pointed out earlier herein, a typical capillary opening or aperture 31 (FIGS. 6 and 6A) located in plane 34a is defined by a multiplicity of intersecting primary fiber-like elements, e.g., elements 701, 702, 703 and 704 (not completely shown), interconnected to one another in plane 34a. Each of the primary fiber-like elements, e.g., element 701, exhibits a substantially uniform U-shaped cross-section along its length. Its cross-section comprises a primary base portion, e.g., primary base portion 701a, located in plane 34a and a primary sidewall portion, e.g., primary sidewall portions 701b, joined to each edge of said primary base portion and extending generally in the direction of the absorbent pad-contacting surface 35 located in plane 34d.

As can be seen from FIGS. 6, 6A and 6B, the intersecting primary sidewall portions of the primary fiber-like elements are interconnected to one another intermediate the first surface 34 and the second surface 35 of the web 30. The primary sidewall portions are further connected to intersecting secondary fiber-like elements, e.g., secondary element 705, which also exhibit a substantially uniform U-shaped cross-section along their length. The cross-section of each secondary element comprises a secondary base portion, e.g., secondary base portion 705a, located in plane 34b intermediate the first surface 34 and the second surface 35 of web 30. The secondary base portions have a secondary sidewall portion, e.g., secondary sidewall portions 705b, joined to each edge thereof. The secondary sidewall portions also extend generally in the direction of the second surface 35 of the web located in plane 34d. As is also apparent in FIGS. 6, 6A and 6B, the secondary sidewall portions are interconnected to the intersecting primary sidewall portions intermediate plane 34b and the second surface 35 of the web located in plane 34d.

In the preferred web embodiment illustrated in FIGS. 6, 6A, 6B and 7, the primary and secondary sidewall portions are further connected to intersecting tertiary fiber-like elements, e.g., tertiary fiber-like elements 706 and 707, which also exhibit a substantially uniform U-shaped cross-section along their length. The cross-section of the tertiary elements comprises a tertiary base portion, e.g., tertiary base portion 706a, located in plane 34c intermediate plane 34b and the second surface 35 of the web. The tertiary fiber-like elements further include a tertiary sidewall portion, e.g., tertiary sidewall portions 706b, joined to each edge of each tertiary base portion. The tertiary sidewall portions also extend generally in the direction of the second surface 35 of the web, and are interconnected to the intersecting primary and secondary sidewall portions intermediate the plane 34c of the tertiary base portions and the plane 34d of the second surface 35 of the web 30.

As can clearly be seen in FIGS. 6, 6A, 6B and 7, the intersecting primary, secondary and tertiary sidewall portions of the fiber-like elements terminate substantially concurrently with one another in the plane of the second surface to form a multiplicity of openings or apertures in the second surface, e.g., apertures 36, 37, 38 and 39.

Referring to FIGS. 6, 6A, 6B and 7, it is clear that the interconnected primary, secondary and tertiary sidewall portions of the fiber-like elements located intermediate the first and second surfaces of the web 30 form a discrete capillary network connecting each of the apertures, e.g., aperture 31, defined by a multiplicity of intersecting primary fiber-like elements, e.g., elements 701, 702, 703 and 704 (not completely shown), in the first surface 34 of the web exclusively with a multiplicity of apertures, e.g., apertures 36, 37, 38 and 39, formed in the second surface 35 of the web by said interconnected primary, secondary and tertiary sidewall portions of said fiber-like elements. As will be appreciated, the capillary networks in the preferred web embodiment of FIG. 6 are of nonuniform cross-section along their length, i.e., intermediate planes 34a and 34d, due to the presence of the secondary and tertiary fiber-like elements. Because the capillary networks connecting each aperture in the first surface 34 of the web exclusively with a multiplicity of apertures in the second surface 35 of the web are of decreasing cross-section in the direction of the second surface, fluid deposited on an aperture, e.g., aperture 31, in the first surface of the web is rapidly transmitted directly to the multiplicity of apertures, e.g., apertures 36, 37, 38 and 39, in said second surface without lateral transmission between adjacent capillary networks.

While the web embodiment generally disclosed in FIGS. 6, 6A and 6B and 7 represents a particularly preferred embodiment of the present invention employing primary, secondary and tertiary fiber-like elements, any number of fiber-like elements may be employed within web structures of the present invention, e.g., quaternary fiber-like elements, quintinary fiber-like elements, etc. Alternatively, the present invention may also be practiced to great advantage by forming resilient three-dimensional webs comprised exclusively of primary fiber-like elements. An embodiment 730 of such a web is illustrated in greatly enlarged condition in FIG. 6C. A multiplicity of apertures, e.g., aperture 731, are formed by a multiplicity of said intersecting fiber-like elements, e.g., elements 701, 702 and 703, interconnected to one another in the first surface 734 of the web. Each fiber-like element comprises a base portion, e.g., base portion 703a, located in plane 734a. Each base portion has a sidewall portion, e.g., sidewall portions 703b, attached to each edge thereof. The sidewall portions extend generally in the direction of the second surface 735 of the web. The intersecting sidewall portions of the fiber-like elements are interconnected to one another intermediate the first and second surfaces of the web, and terminate substantially concurrently with one another in the plane 734b of the second surface. In a particularly preferred embodiment, the interconnected sidewall portions terminating substantially concurrently with one another in the plane of said second surface form apertures in the second surface of the web. If the sidewall portions of the fiber-like elements are oriented substantially perpendicular to the base portions of said elements, the apertures 731' formed in the second surface will be approximately the same size as the apertures 731 in the first surface of the web. Alternatively, the sidewall portions may be angled with respect to said base portions to produce apertures 731' in said second surface which are smaller than the apertures 731 in the first surface of the web. In the latter case, the capillary network formed by said interconnected sidewall portions is of decreasing cross-section in the directon of said second surface. As with the embodiment of FIG. 6, this decreasing cross-section aids in transporting fluids deposited on the first surface of the web directly to the second surface of said web without lateral transmission of said fluids between adjacent capillary networks.

Figure 6C:
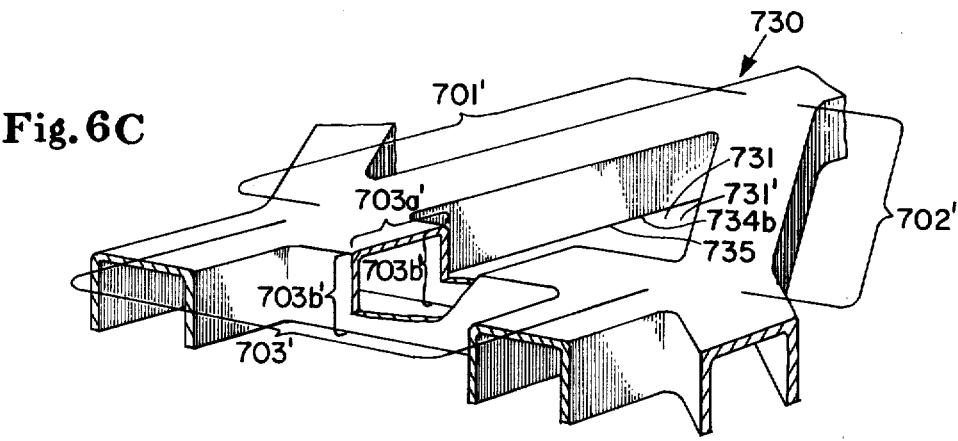
FIG. 6C is an enlarged, partially segmented, perspective illustration of an alternative web of the present invention.
Figure 6D:
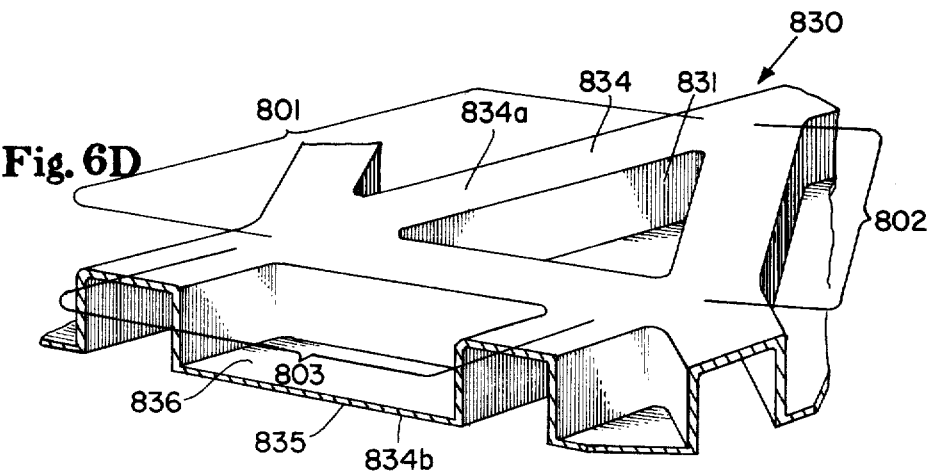
FIG. 6D is an enlarged perspective illustration of yet another web of the present invention.

FIG. 6D is a greatly enlarged perspective illustration of still another web embodiment 830 of the present invention. The web 830 is in most respects similar to the web 730 shown in FIG. 6C. The key difference is that the interconnected sidewall portions of the intersecting fiber-like elements, e.g., elements 801, 802 and 803, which terminate substantially concurrently with one another in the plane 834b of the second surface 835 are interconnected to the periphery of a planar member, e.g., planar member 836. Accordingly, the sidewall portions do not terminate to form apertures in said second surface. Thus, the apertures 831 formed in the plane 834a of the first surface 834 are not in fluid communication with the second surface 835 of the web 830. Webs of the type generally shown in FIG. 6D may be debossed without aperturing across their entire surface, or only in predetermined areas, as desired. Such webs are particularly useful in applications where a fiber-like appearance and tactile impression are desired, but fluid permeability is not desired.

As will be appreciated, the substantially U-shaped fiber-like elements utilized in webs of the present invention may be substantially straight along their entire length. Alternatively, they may be curvilinear, they may comprise two or more substantially straight segments or they may be otherwise oriented in any desired direction along any portion of their length. Furthermore, the aforementioned shapes may be combined in any desired fashion to produce whatever fiber-like pattern is desired. Regardless of the shape ultimately selected, the substantially uniform U-shaped cross-section along the length of the interconnected fiber-like elements helps impart resilience to fiber-like plastic webs of the present invention.

Figure 7:
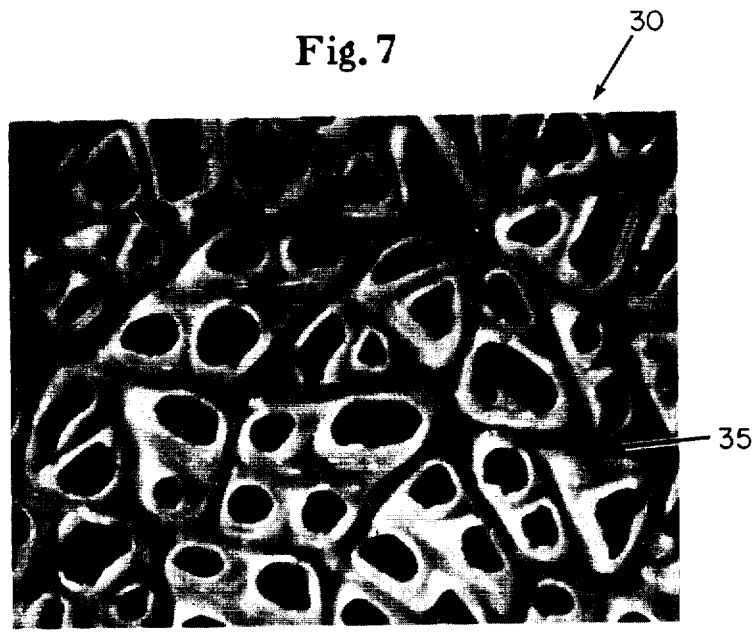
FIG. 7 is a plan view photograph enlarged approximately 27 times of the lowermost surface of the web illustrated in FIG. 6.

FIG. 7 is a plan view photograph enlarged approximately 27 times of the fiber-like web 30 shown in FIG. 6, taken from the lowermost surface 35 of the web.

From FIG. 6 it should be noted that adjacent capillary networks, while exhibiting a generally similar regulated continuum of capillary openings of successively smaller size in the direction of the lowermost surface 35 of said web, are dissimilar in overall shape and exact manner of subdivision. Accordingly, the resultant plastic web 30 exhibits much more of a random three-dimensional fiber-like appearance and tactile impression to the user than has been obtainable by prior art methods and apparatus. The increased fluid permeability and finer detail of the fiber-like plastic web 30 of FIG. 6 are clearly apparent when contrasted to a prior art plastic web 20 of the type illustrated in FIG. 4.

A comparison of the wearer-contacting surface 34 of a preferred plastic web 30 of the present invention, the wearer-contacting surface 24 of the prior art plastic web 20 illustrated in FIG. 4 and the wearer-contacting surface 14 of the prior art nonwoven fibrous web 10 illustrated in FIG. 2 reveals a much greater similarity between the fluid-pervious plastic web 30 of the present invention and the prior art nonwoven fibrous web 10 illustrated in FIG. 2 than between the prior art plastic web 20 and the nonwoven fibrous web 10. This is likewise true with respect to a comparison of the lowermost surface 35 of a plastic web 30 of the present invention, the lowermost surface 25 of the prior art plastic web 20 illustrated in FIG. 5 and the lowermost surface 15 of the prior art nonwoven fibrous web 10 illustrated in FIG. 3.

As should be readily apparent from the foregoing, the present invention, in a particularly preferred embodiment, combines the desirable fluid transport and anti-rewet properties provided by the tapered capillaries 21 of prior art plastic web 20 with the air permeability, wet and dry resilience, three-dimensionality, and, at least to a degree, the fiber-like feel and appearance of prior art nonwoven fibrous web 10 in a single, three-dimensional, resilient fluid-pervious plastic web 30.

Figure 5:
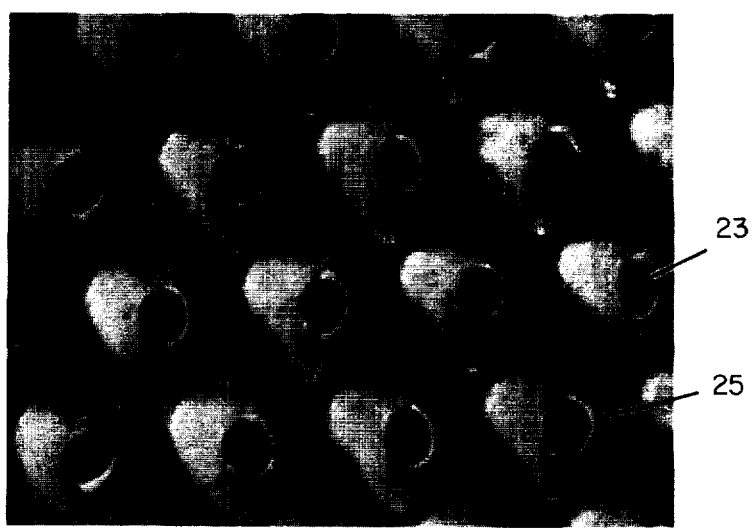
FIG. 5 is a plan view photograph enlarged approximately 27 times of the vacuum formed plastic web illustrated in FIG. 4, but taken from the absorbent pad contacting surface of the web.

To further demonstrate the improved functional characteristics exhibited by plastic webs of the present invention, samples of a prior art non-woven web as generally shown in FIGS. 2 and 3 (Example I), a prior art elastic web having tapered capillaries as generally shown in FIGS. 4 and 5 (Example II) and a fiber-like plastic web of the present invention as generally shown in FIGS. 6 and 7 (Example III) were subjected to strikethrough, surface wetness, permeability and tensile strength testing.

The prior art non-woven web (Example I) was comprised of non-woven polyester fabric such as is available from The Kendall Company of Walpole, Massachusetts. The non-woven web, which had a maximum basis weight of approximately 18 grams of per square yard, exhibited a multiplicity of depressed areas as generally described in U.S. Pat. No. 4,041,951, issued to Sanford on Aug. 16, 1977 and incorporated herein by reference.

The prior art plastic web having tapered capillaries (Example II) was comprised of 2.5 mil thick, low slip, unembossed polyethylene available from Visqueen Division of Ethyl Corporation of Baton Rouge, Louisiana under the specification Visqueen White #1850. The tapered capillaries exhibited a base opening diameter of about 0.040 inches, a height of about 0.012 inches, and an apex opening diameter of approximately 0.016 inches. The prior art tapered capillary film exhibited approximately 625 evenly spaced tapered capillaries per square inch.

The fiber-like plastic web of the present invention (Example III) was comprised of 2.5 mil thick polyethylene film of the type utilized to form the web of Example II. The pattern exhibited by the Example III web was identical to that illustrated in FIGS. 6 and 7, which are enlarged approximately 27 times actual size.

The webs of Examples II and III were formed under similar conditions. Planar metal segments of the respective forming surfaces were preheated in a 225° F. oven, and the films were heated to a temperature near their melting point prior to bringing them in contact with the forming surfaces. The lowermost sides of the respective forming surfaces were thereafter exposed to a level of vacuum sufficient to draw the films resting on their uppermost surfaces into conforming contact therewith. Perforation of the films was carried out by directing air heated to a temperature of approximately 800° F. against the uppermost surfaces of the films while the lowermost surfaces of the films were exposed to vacuum on their respective forming surfaces. The films were thereafter allowed to cool on the forming surfaces and manually removed therefrom.

Several samples of each of the materials described in Examples I, II and III were thereafter subjected to comparative testing for strikethrough, surface wetness, air permeability and tensile strength. The tests conducted on the webs described in Examples I, II and III are hereinafter described in greater detail.

STRIKETHROUGH

Strikethrough, as utilized herein, is a measure of the time required for a given volume of surface-applied liquid to enter, or "strikethrough", a topsheet material into an underlying absorbent structure. In the present series of tests it is a measure of the time in seconds to completely drain 5 milliliters of simulated urine solution having a surface tension of 45 dynes/centimeter from a one inch diameter by ⅜ inch deep cavity having a multiplicity of holes in its lowermost surface. The cavity is integrally formed in a 4 inch×4 inch strikethrough plate which is placed on a 4 inch by 4 inch composite structure comprising the topsheet being tested and an absorbent element consisting of a layer of airlaid comminuted wood pulp fibers enveloped between a pair of wet strength tissue plies. The wearer-contacting surface of the topsheet sample is oriented face-up. An electric timer is started by the simulated urine solution contacting a pair of spaced electrodes in the aforedescribed cavity. The timer automatically shuts off when all of the simulated urine solution has drained from the cavity and into the absorbent element. Times are reported in seconds.

SURFACE WETNESS

In order to compare the surface wetness characteristics of Examples I, II and III, a test designed to measure the amount of liquid which emerges from an absorbent structure, such as the disposable diaper 1 shown in FIG. 1, through a topsheet to cause wetness on the surface of the topsheet was conducted. The amount of moisture drawn through the topsheet is termed "surface wetness" and serves as an estimate of how dry the wearer's skin would remain if placed in contact with the absorbent structure.

Briefly, the test comprises wetting a 4 inch by 4 inch sample of each topsheet material while superposed, wearer-contacting side up, on a standardized absorbent element preferably comprising a layer of airlaid comminuted wood pulp fibers enveloped between a pair of wet strength tissue plies with a simulated urine solution having a surface tension of approximately 45 dynes/centimeter until the absorbent portions of the structure, i.e., the absorbent element, including the wet strength envelope tissue has become saturated. In the present series of tests saturation did not occur until a loading factor of 4.8 had been reached, i.e., until the absorbent sample contained 4.8 grams of simulated urine solution per gram of absorbent sample. A uniform pressure loading of 0.5 p.s.i. is applied to each sample for a period of 3 minutes so that the fluid is uniformly distributed throughout the sample. The pressure is momentarily removed, a preweighed sample of filter paper approximately 15 centimeters in diameter is inserted over the uppermost surface of the topsheet of the absorbent sample, and the predetermined pressure loading is reapplied to the sample for a period of 2 minutes. The filter paper is then removed and reweighed, and the amount of fluid absorbed by the filter paper is termed the "surface wetness" of the sample. Results are expressed in grams of fluid absorbed by the filter paper. As should thus be apparent, a lower "surface wetness" number is indicative of a dryer surface feel.

AIR PERMEABILITY

Air permeability of the sample webs, which is an indirect measure of breathability and comfort, was determined by placing a one inch diameter sample of each web material on a Frazier High Pressure Differential Air Permeability Tester, such as is available from Frazier Precision Instrument Company of Gaithersburg, Maryland. A Frazier No. 8 orifice plate was utilized on Examples I and III, while a No. 4 orifice plate was used on Example II to avoid blowing the fluid from the attached manometer. Results were obtained directly from the manometer and converted by means of a standardized chart to provide air flow readings in cubic feet of air per square foot of web material per minute at 30 inches Hg, 70° F., 65% Relative Humidity, the conditions underwhich the tests were performed.

TENSILE STRENGTH

All tensile tests were made on an Instron Model 1122 Tensile Tester, such as is available from the Instron Corporation of Canton, Massachusetts. Tests were conducted by clamping a one inch wide by two inch long sample in the tester at an initial jaw spacing of one inch. A crosshead speed of one inch per minute was applied until the sample ruptured. Readings at the point of rupture were taken from the Instron's chart recorder, and are expressed in terms of grams per inch of sample width.

Results of the aforedescribed tests reported in Table I represent the average value of all tests actually conducted for each Example. Between 2 and 5 tests were conducted for each Example.

TABLE I

| Test | Example I (Prior art non-woven fabric web as shown in FIG. 2 and 3) | Example II (Prior art plastic web having tapered capillaries as shown in FIG. 4 and 5) | Example III (Fiber-like plastic web of the present invention as shown in FIG. 6 and 7) |
|---|---|---|---|
| Strike-through (time in seconds) | 1.57 | 2.68 | 3.45 |
| Surface wetness (grams of simulated urine absorbed by filter paper) | 1.66 | 0.03 | 0.03 |
| Air permeability (cubic ft. of air per sq. ft. of material per minute at 30 inches Hg, 70° F., 65% Relative Humidity | 841 | 185 | 677 |
| Tensile strength/ machine direction (grams per inch) | 2,970 | 1,532 | 719 |
| Tensile strength/ cross-machine direction (grams per inch | 291 | 1,029 | 577 |

From the data in Table I it is clear that the directional fluid handling characteristics of the fiber-like plastic web of Example III closely approximate those exhibited by the prior art plastic web of Example II. While the performance of neither of the plastic webs is quite equal to that of the non-woven fabric web of Example I in terms of strikethrough, experience has demonstrated that the strikethrough characteristics exhibited by any of the webs considered in Examples I, II and III are quite satisfactory for use as a disposable diaper topsheet. Furthermore, it is critical to note that both plastic webs exhibit tremendous improvement over the non-woven web in terms of surface wetness performance, a characteristic which impacts significantly on wearer comfort. Hence their use as a topsheet is highly preferred in structures such as disposable diapers, sanitary napkins and the like, wherein it is desired to isolate the wearer's skin from fluids absorbed into the absorbent element of the structure.

The desirable surface wetness characteristics exhibited by the web of Example III are even more astounding when the results of the air permeability tests are compared. The air permeability of the fiber-like web of Example III is approximately 3–4 times that of the prior art tapered capillary web of Example II, and closely approaches that of the non-woven fabric web of Example I.

While the machine-direction tensile strength of the plastic web of Example III is only about one half that of the prior art plastic web of Example II and only about one fourth that of the non-woven fabric web of Example I, it is noteworthy that its crossmachine direction tensile strength is approximately double that of the non-woven fabric web of Example I. Although the web of Example III exhibits adequate tensile strength for use as a topsheet in most disposable absorbent bandage applications, the reduction in machine-direction tensile strength can, if desired, be compensated for by any of various reinforcing means well known in the art. In the case of a disposable diaper wherein the waistbands are subject to greatest tensile loading as the structure is being applied, this could be accomplished by any of various means well known in the art, i.e., reinforcing the waistband areas with beads of adhesive, leaving the waistband areas of the topsheet imperforate (this would not adversely affect the diaper's performance since body fluids are not normally discharged in this area), adding an independent reinforcing material in the waistband area, etc.

From the foregoing it is clear that plastic webs of the present invention can be made to exhibit desirable properties and characteristics which have been unachievable in a single prior art structure, i.e., the strikethrough and surface wetness characteristics of prior art plastic webs employing tapered capillary openings in conjunction with an air permeability, softness, tactile impression, and handle approaching those of prior art non-woven fabrics.

Furthermore, plastic webs of the present invention may be particularly advantageous in situations where the point of fluid entry is reasonably well defined, such as in sanitary napkins. Fiber-like webs of the present invention may, if desired, be made to exhibit the overall three-dimensional pattern of the fiber-like forming surface, but perforated only in the area where body fluids are likely to be discharged. The discharged fluids are allowed to enter the absorbent element of the structure through the perforated areas of the web, while the imperforate areas of the web serve not only to effectively contain, but also to mask or hide the fluids absorbed by the structure. Because the unsightly appearance of the absorbed body fluids is masked, the user feels more comfortable in wearing the structure until its full absorptive capacity has been utilized.

Figure 8:
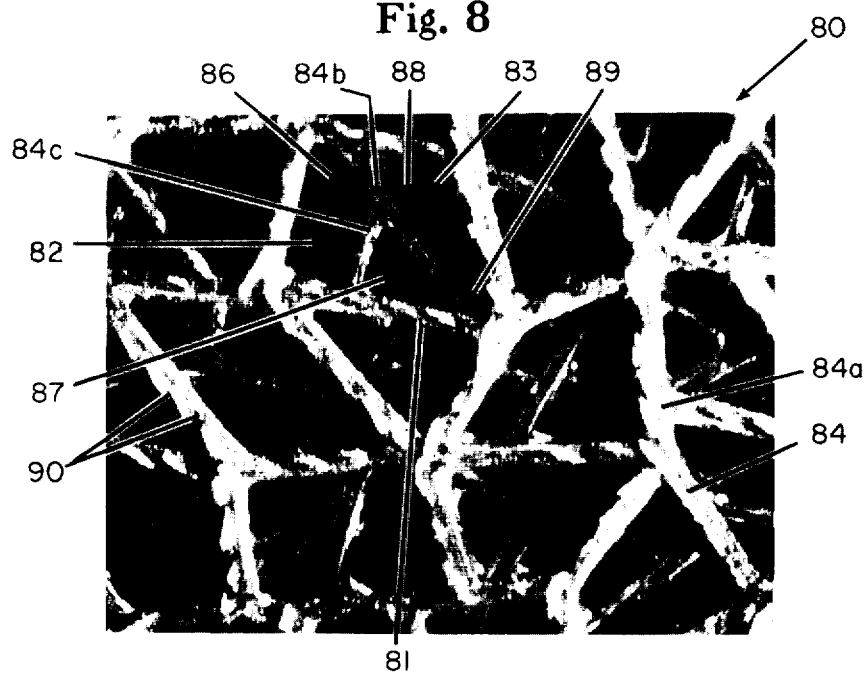
FIG. 8 is a plan view photograph enlarged approximately 27 times of a planar segment of a photoetched laminate structure of the type utilized to form plastic webs of the type generally illustrated in FIGS. 6 and 7.

FIG. 8 is a plan view photograph enlarged approximately 27 times of the film contacting surface 84 of a photoetched laminate structure 80 utilized to vacuum form an initially impervious, substantially planar, heated plastic film to produce a fluid-pervious fiber-like web 30 of the type generally illustrated in FIGS. 6 and 7. A comparison of FIG. 8 with the fiber-like plastic web 30 shown in FIG. 6 reveals the correspondence of capillary opening 31 in the uppermost plane 34a of plastic web 30 to opening 81 in the uppermost plane 84a of the photoetched laminate structure 80. Likewise, capillary openings 32 and 33 in intermediate plane 34b of plastic web 30 correspond to intermediate openings 82 and 83, respectively, in intermediate plane 84b of photoetched laminate structure 80. Finally, capillary openings 36, 37 and 38, 39 in lowermost plane 34c of plastic web 30 correspond to openings 86, 87 and 88, 89, respectively, in lowermost plane 84c of photoetched laminate structure 80.

In the particularly preferred embodiment of the present invention shown in FIG. 8, the uppermost surface of photoetched laminate structure 80 located in uppermost plane 84a is provided with a fine scale microtexture comprising a multiplicity of generally parallel V-shaped grooves 90 which help to create a random, non-planar surface appearance in the processed plastic web. The ridges and valleys formed by the V-shaped grooves 90 tend to minimize the web's gloss. This is preferably accomplished by utilizing a striated pattern exhibiting whatever shape or effect is desired in the resist coating applied to the uppermost or film-contacting surface of the lamina during the photoetching process. When the lamina is photoetched, the uncoated striations permit partial etching of the uppermost surface to form the V-shaped grooves 90 across the entire uppermost surface of the resultant photoetched lamina. As will be appreciated by those skilled in the art, any of various techniques known in the art for providing the desired degree of surface roughness may be utilized in conjunction with lamina of the present invention. While the surface roughening treatment described herein has been limited to the uppermost lamina of the structure shown in FIG. 8, it may, if desired, also be applied to other lamina within the stack.

Figure 9:
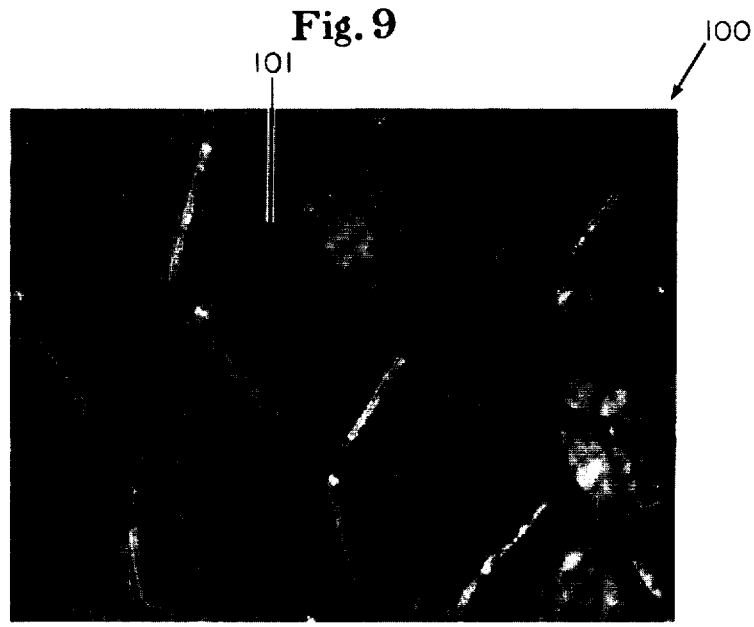
FIG. 9 is a plan view photograph enlarged approximately 27 times of an individual lamina of the type utilized in the uppermost portion of the photoetched laminate structure illustrated in FIG. 8.

FIG. 9 is a plan view photograph enlarged approximately 27 times of an individual lamina 100 of the type employed in the uppermost portion, i.e., that portion intermediate planes 84a and 84b, of the photoetched laminate structure 80 illustrated in FIG. 8. As is apparent from an inspection of the photograph, opening 101 corresponds to opening 81 in laminate structure 80. Note, however, that the V-shaped grooves 90 which provide a microtexture effect in the uppermost plane 84a of the laminate structure 80 are not present since the lamina 100 is not the uppermost lamina in the structure.

Figure 10:
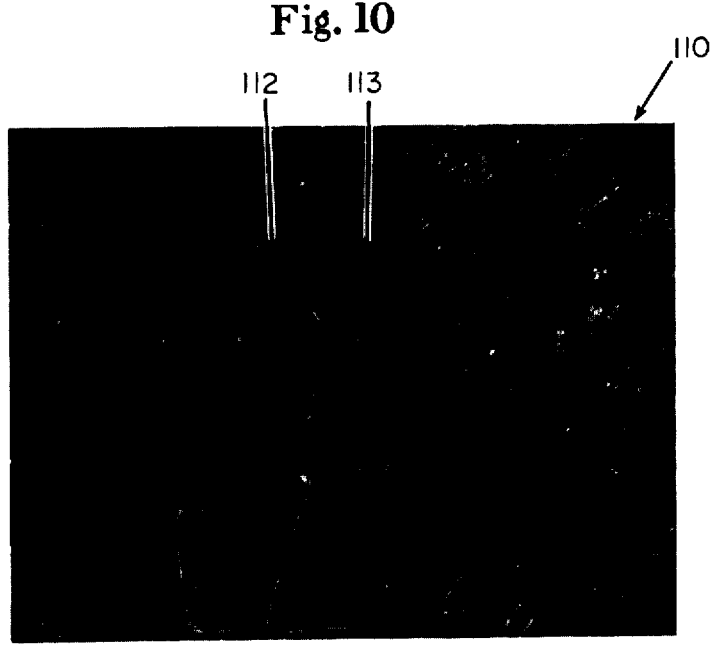
FIG. 10 is a plan view photograph enlarged approximately 27 times of yet another individual lamina of the type utilized in the intermediate portion of the photoetched laminate structure illustrated in FIG. 8, the peripheral outline of each group of openings in said lamina being similar to the outline of the corresponding openings in the lamina illustrated in FIG. 9, but further subdivided.

FIG. 10 is a plan view photograph enlarged approximately 27 times of an individual lamina 110 of the type generally found intermediate planes 84b and 84c of the photoetched laminate structure 80 illustrated in FIG. 8. Note the presence of openings 112 and 113 corresponding to openings 82 and 83 in the photoetched laminate structure 80.

FIG. 11 is a simplified, partially exploded, perspective illustration of a laminate structure 120 generally similar to that of FIG. 8. The laminate structure 120 is comprised of a stack of individual lamina 130, 131, 132, 133 and 134. Each lamina has a pattern of openings therein. Lamina 132, 133 and 134 are identical to one another. In practice it is typical to employ several identical lamina superposed upon one another to provide sufficient depth of pattern in each dissimilar portion of the laminate structure. However, for simplicity of illustration a single uppermost lamina 130 and a single intermediate lamina 131 are shown. Lamina 130 exhibits a patterned arrangement of openings 121 which when superposed on lamina 131 align generally with the peripheral border formed by each pair of openings 122, 123. Similarly, the peripheral borader formed by each group of openings 126, 127, 128 and 129 in lamina 132 are generally aligned with the peripheral border formed by openings 122 and 123, respectively, in lamina 131 and opening 121 in lamina 130. From the foregoing, it is readily apparent how intricate three-dimensional geometric structures can be created in nearly any pattern which is desired. It should further be apparent that the resultant three-dimensional structure, in most instances, in not susceptible of machining or weaving due to inherent limitations in the machining and weaving processes. For example, non-uniform cross-sections in which the open area is greatest near the center of the laminate structure's thickness are feasible. This can be done by employing centrally located lamina having open areas greater than those of the lamina employed for the outermost layers.

In order to construct laminate forming surfaces for less complex webs of the type generally disclosed in FIGS. 6C and 6D, i.e., webs comprised exclusively of intersecting primary fiber-like elements and having interconnected sidewall portions which are substantially perpendicular to the surfaces of the web, the laminae utilized to construct the forming surface must contain identical registered patterns of openings. It is then only necessary to superpose a sufficient number of such laminae to provide the desired pattern depth. Alternatively, where sidewall portions which are non-perpendicular to the surfaces of the web are desired, laminae exhibiting similar patterns of dissimilar size may be stacked with their patterns in register with one another. The latter approach may, if desired, be utilized to produce capillary networks exhibiting a substantially uniform taper along their length.

FIG. 12 illustrates a simplified embodiment of a laminate structure 140 employing an approach of the aforementioned type. Laminate structure 140 could, if desired, be utilized to provide a surface suitable for debossing and perforating an initially imperforate, substantially planar plastic film to produce a fluid-pervious web exhibiting a pattern of the type generally illustrated in FIGS. 4 and 5. The laminate structure 140 is comprised of a stack of individual lamina 150, 151, 152, 153 and 154. Each lamina has a pattern of regularly spaced openings therein. The pattern of openings 141 in lamina 150 is concentrically aligned with the pattern of openings 142 in lamina 151, the pattern of openings 143 in lamina 152, the pattern of openings 144 in lamina 153 and the pattern of openings 145 in lamina 154. The diameter of openings 141 is greater than the diameter of openings 143, etc., all the way through laminae 153 and 154. Thus the resultant laminate structure 140 provides a regulated pattern of conical openings extending from the uppermost lamina 150 through the lowermost lamina 154. If desired, the uppermost surface of lamina 150 could also be provided with a microtexture effect, i.e., V-shaped grooves as generally indicated at 90 in the embodiment in FIG. 8, to provide the resultant plastic web with a microtextured effect. Thus, in addition to providing a vehicle for constructing forming surfaces which cannot be formed by prior art means, the lamination technique generally disclosed herein may be utilized as an improved vehicle for constructing forming surfaces which are capable of construction by slower, more expensive and less precise prior art means.

While photoetched and other types of laminate structures per se have for some time been generally known in the art, application of the lamination technique, particularly the photoetched lamination technique, in accordance with the present invention to create novel, continuous forming surfaces having unique properties and characteristics unachievable by prior art machining and/or weaving techniques is of tremendous commercial significance in that it virtually frees the plastic web forming industry from the prior art machining and/or weaving limitations inherent in prior art film forming surfaces.

One known prior art process for constructing a laminate structure is disclosed in U.S. Pat. No. 2,926,490 issued to Eaton et al. on Mar. 1, 1960, said patent being hereby incorporated herein by reference. Eaton et al., in the disclosed embodiment, teaches a method of producing a laminated thrust chamber built up from stacked thin laminations having straight axial passages formed therein. Briefly, the disclosed method of producing the laminated thrust chamber comprises four principle steps: (1) fabrication of the complete series of matching laminations; (2) preparation of the laminations for joining; (3) assembly of the laminations; and (4) joining the assembled laminations. According to the teachings of Eaton et al., the laminations may be formed by any suitable process such as punching from sheet material, casting, or etching. The particular material used may be either a suitable metal or a refractory material. The laminations are thereafter prepared for the selected method of joining, which includes suitable cleaning and surface preparation. For instance, if brazing is to be the method employed, their meeting surfaces are coated with braze metal. The individual laminations are then stacked in the proper order to produce the internal contour desired in the nozzle area of the structure and arranged rotationally to obtain proper longitudinal registration of the perforations that form the continuous longitudinal coolant passages in the resultant thrust chamber. The stacked laminations are finally fixtured in the desired arrangement and permanently joined by the chosen method, such as by welding, furnace brazing, or dip brazing to form a thrust chamber exhibiting the desired internal contour as well as continuous, contour-conforming passages for the circulation of coolant liquid.

Similarly, a prior art process for constructing a laminar mesh suggested for use as a holding fixture or for use as a light deflection mask is disclosed in U.S. Pat. No. 3,174,837 and 3,390,447 issued to Mears on Mar. 23, 1965 and July 2, 1968, respectively, said patents being hereby incorporated herein by reference. The Mears patents disclose a method for making a flat rigid laminar mesh having an array of accurately aligned apertures, each of which provides a line of sight opening passing through the laminar. In the disclosed process, the individual plates are electroformed or photoetched with patterns of apertures therein, coated with solder, stacked on alignment pins so that the apertures are centered with respect to one another and bonded by the application of heat and pressure without clogging the apertures in the resultant structure.

Still another known prior art process for constructing a photoetched laminate structure is disclosed in U.S. Pat. Reissue 29,524 reissued to Spencer on Jan. 24, 1978, said patent being hereby incorporated herein by reference. The Spencer patent discloses a method for constructing a multilayer porous material particularly suited for use in filtering and turbine cooling applications. In the disclosed embodiment, a plurality of lamina, each having a parallel slot series formed therein, is stacked with the respective adjacent slot series overlapping and extending transversely to each other. The stack is then bonded together to form a porous laminate. In a disclosed variation, the slots in one or more of the lamina are tapered to create a variable porosity in the resultant laminate structure. Basically, the disclosed process includes the steps of photoetching metal sheets to create the slot pattern, stacking a plurality of the sheets together with the slots in adjacent sheets extending transversely to each other, diffusion bonding the stacked sheets to form a porous laminate, and calendering the finished laminate structure to modify or adjust its permeability.

In a particularly preferred embodiment of the present invention, photoetched laminate structures such as the one illustrated in FIG. 8 are comprised of a multiplicity of photoetched laminar stainless steel plates, each plate or each series of plates exhibiting a pattern of openings dissimilar to the adjacent plate or series of plates. The laminar plates are bonded to one another at points of contact to form an integral three-dimensional structure at whatever scale is desired for the particular application. The fineness of the pattern is of course subject to strength limitations inherent in the laminar plates. These inherent strength limitations control the minimum cross-sectional size of any structural member remaining within a given plate after the photoetching process has been carried out.

The preferred method of manufacturing laminate structures of the present invention includes the step of photoetching the desired patterns into the individual lamina. This process involves the coating of one or both sides of the lamina with a resist material in the areas to remain solid. This coating can be done in several ways well known in the art including silk screen, painting, or by photographic means. If a surface microtexture is desired in the resultant lamina, the resist coating applied to the surface may include a fine pattern of striations or the like. This is followed by a chemical etching process which dissolves the uncoated material to thus create the individual lamina. Inasmuch as this process is known to those skilled in the art, it is not felt necessary to set forth herein a complete detailed description thereof. While photoetching, as outlined above, is generally preferred, it is of course recognized that other forming methods, such as precision stamping, could be used in some cases where the scale of reproduction and the fineness of the pattern will permit.

The photographic coating technique, which is particularly preferred in the practice of the present invention, permits creation of patterns specifically designed to provide the precise features desired in the resultant laminate, and consequently in the plastic web formed thereon, at a scale sufficiently large to be accurately drawn. The finished larger scale drawings may then be photographically reduced in size to produce the identical pattern at whatever scale or degree of fineness is desired. This photographic technique is particularly desirable in a fiber-like laminate structure of the type shown in FIG. 8, wherein the continuum of capillary networks of steadily decreasing size is created by sequential subdivison of the openings 81 originating in the uppermost plane 84a of the laminate structure 80.

The stainless steel from which the individual lamina are preferably comprised supplies much of the strength necessary in the extremely fine sections of a design such as the one shown in FIG. 8. The individual lamina, which are typically comprised of 410 stainless steel, may vary in thickness from about 1 mil to about 5 mils in any given laminate structure. Furthermore, identical lamina may be superposed upon one another to provide whatever depth or thickness is desired for any given pattern of openings within the laminate structure. To facilitate bonding, the individual lamina are preferably electroplated with a coating of pure copper which may vary in thickness from between about 0.01 mils to about 0.1 mils, depending upon the fineness of the pattern in the lamina and the desired degree of bonding in the resultant laminate structure. In a particularly preferred embodiment, individual lamina of the present invention are first cleaned and struck with a coating of nickel having a thickness on the order of 0.01 mils to ensure more effective adherence of the copper plate to the stainless steel. While in most instances every lamina in the stack is electroplated with copper, it has been found preferable where extremely fine or delicate patterns are involved to electroplate only every other lamina in the stack to avoid an excessive buildup of copper in the resultant laminate structure.

After electroplating with copper, the individual lamina are stacked in the sequence and orientation desired to produce the resultant three-dimensional microstructure, and the stack is preferably pinned through registration holes which are photoetched in the laminar plates at the same time the pattern is etched. To avoid disruption of the three-dimensional pattern exhibited by the laminate structure, registration holes may be provided either in the borders of the desired pattern or on separate break-away borders of the laminate structure. The pins utilized to stack the laminates are also preferably comprised of stainless steel to minimize thermal distortion, and are the exact diameter of the registration holes. A ceramic collar is preferably slipped over each pin on top and bottom of the stack of individual lamina and a stainless steel sleeve is then crimped onto the exposed portion of the pins to hold the stack tightly together in proper registration. Since the brazing operation bonds the stainless steel pins to the resultant structure, their use is generally limited to situations where they may be left in place and their ends ground off, or to situations employing break-away borders. In the event the pins must be removed after brazing, ceramic pins and ceramic collars must be employed.

After pinning, the laminate stack is subjected to a furnace brazing operation to bond the stack of individual lamina into an integral structure. A honeycomb pattern, silicon nitride ceramic plate is preferably placed adjacent the uppermost and lowermost surfaces of the laminate stack, and a loading sufficient to provide good bonding but not so great as to cause distortion or deformation of the laminate stack is applied to the ceramic plates during the furnace brazing operation. To ensure the flattest possible surfaces being applied against the laminate stack, the laminate-contacting surfaces of the honeycomb plates are preferably surface ground. The honeycomb ceramic material allows uniform heating of the surfaces of the laminate structure, thereby ensuring uniform bonding throughout the contacting portions of the stack of laminar plates. One material found particularly suitable for this purpose is the silicon nitride honeycomb ceramic available from The Norton Company of Worcester, Mass. While the material is available in various honeycomb sizes, one half inch thick sheets having honeycomb openings measuring approximately 1/16 inch across the flats were employed on the laminate structure shown in FIG. 8. An alternative material also found suitable for this purpose is a cordierite ceramic honeycomb material available from the General Refractories Company of Philadelphia, Pa.

Furnace brazing of the laminate stack to bond the individual lamina to one another is preferably carried out in a brazing furnace utilizing a pure hydrogen atmosphere to prevent oxidation of the copper. In a particularly preferred embodiment, the laminate stack assembly is placed in the furnace and heated to approximately 1800° F. until stabilized, i.e., until flashing of the copper plating is initiated. The furnace temperature is then elevated to approximately 2,025° F. and held for approximately three minutes to achieve a more normalized condition of the copper. This improves the ductility of the resultant laminate structure. Normalizing is preferably followed by rapid cooling, i.e., about 15 minutes, to approximately 200° F. The stacked laminate assembly is thereafter removed from the brazing furnace and allowed to air cool to room temperature.

It should be noted that in furnace brazing operations, it is preferable that all the lamina in a given stack be of the same grade of stainless steel and that the grain of each lamina be aligned throughout the stack to minimize the chance of distortion in the resultant laminate structure.

In photoetched laminate structures where extremely fine detail is present, a portion of the copper may tend to fillet some of the sharp corners of the three-dimensional microstructure during the furnace brazing operation. This filleting copper may be subsequently stripped out by putting the laminate assembly into a chromic acid bath for a period of time sufficient to remove the excess copper, said period of time being determined by visual observation. The stacked laminate is thereafter reinserted into the brazing furnace until it reaches a temperature of approximately 1800° F. and is held at that temperature for a period of about 2 minutes to even out the remaining copper plating.

In a particularly preferred embodiment of the present invention, the resultant photoetched laminate structures are rolled by conventional techniques into a tubular forming member 160, as illustrated generally in FIG. 13. Contrary to expectations, it has been determined that rolling the planar laminate structure into a tubular shape does not tend to cause delamination of the stucture, provided the furnace brazing operation has been properly carried out. Where extremely intricate patterns are present in the laminate structure, it has been learned that placing a thin sheet of urethane on opposite sides of the laminate structure as it is passed through the metal rolls will minimize the change of injury to the fine pattern while rolling the member into the desired tubular shape.

The outermost surface 164 of the tubular forming member 160 is utilized to form the plastic web brought in contact therewith while the innermost surface 165 of the tubular member generally does not contact the plastic web during the forming operation. The tubular member 160 may, in a preferred embodiment of the present invention, be employed as the forming surface on debossing/perforating cylinder 555 in a process of the type generally illustrated in FIG. 16 and described in detail in the aforementioned patent application of Malcolm B. Lucas and Robert H. Van Coney entitled "METHOD OF AND APPARATUS FOR DEBOSSING AND PERFORATING A RUNNING RIBBON OF THERMOPLASTIC FILM", Ser. No. 733,961, filed Oct. 19, 1976, issued on Apr. 24, 1979 as U.S. Pat. No. 4,151,240, said application being incorporated herein by reference.

A significant advantage offered by photoetched laminate forming surfaces of the present invention when contrasted to prior art machined or woven forming surfaces is the ability to join the free ends of a single photoetched laminate section to one another or the ability to join one photoetched laminate section to another photoetched laminate section of similar pattern with substantial continuity in the three-dimensional pattern existing throughout the structure in the area of joinder. This technique may also be employed to join a multiplicity of small sections of similar photoetched laminate structures to one another where, for one reason or another, it is impractical to integrally form the individual lamina in large enough size.

Figure 14:
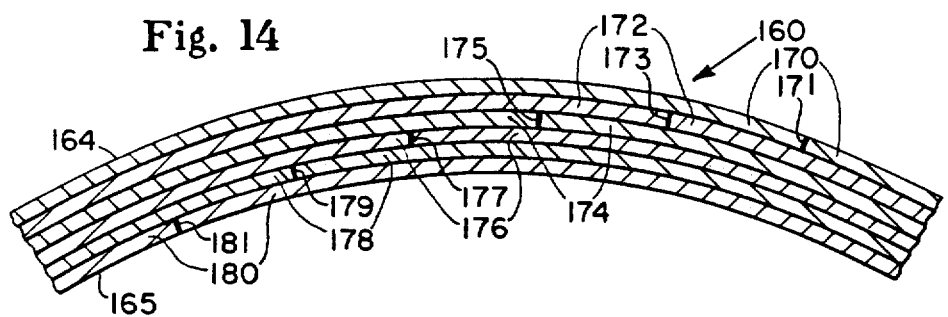
FIG. 14 is an enlarged, simplified cross-sectional view taken along section line 14—14 of FIG. 13 illustrating a preferred lap seaming technique for joining the free ends of the photoetched laminate structure to one another without substantially disrupting the three-dimensional pattern of the laminate structure in the area of joinder.

FIG. 14 which is a simplified cross-sectional view taken along section line 14—14 of FIG. 13 illustrates one preferred manner of joining the free ends of tubular member 160 to one another to provide an integral tubular structure exhibiting substantially no discontinuity in the three-dimensional pattern in the area of joinder. In the particularly preferred embodiment shown in FIG. 14, a lap seam is created by allowing each free end of the planar photoetched laminate structure from which tubular member 160 is formed to project in a manner resembling a series of parallel stairsteps. Since the pattern exhibited by each photoetched lamina is precisely regulated and highly repeatable, rolling the planar laminate structure into a tubular shape causes the mating free ends to align with one another in stairstep fashion as illustrated in FIG. 14. Thus, if the slight differences in radius of curvature for each successive lamina in the stack are ignored, corresponding parts of the pattern employed in lamina 170 mate with one another at 171; corresponding parts of the pattern employed in lamina 172 mate with one another at 173; corresponding parts of the pattern employed in lamina 174 mate with one another at 175; corresponding parts of the pattern employed in lamina 176 mate with one another at 177; corresponding parts of the pattern employed in lamina 178 mate with one another at 179; and corresponding parts of the pattern employed in lamina 180 mate with one another at 181. As is apparent from FIG. 14, no individual lamina seam is radially aligned with another, yet the three-dimensional pattern of the tubular member 160 existing between the outermost surface 164 and the innermost surface 165 is substantially identical at any point along the periphery of the tubular member, including the area of joinder. Furthermore, the resultant seam has much greater strength than a radially aligned butt joint due to the reinforcing effect of one lamina on its adjacent lamina. Joinder of the lap seam shown in FIG. 14 is preferably carried out by applying a low melting point, i.e., under 1000° F., metal bonding alloy to the area of joinder utilizing either a torch or a brazing furnace similar to that generally described in connection with lamination area of joinder while at a temperature which is sufficiently low that it does not adversely affect the copper bonding within the laminate structure per se. Alternatively, the joint could be furnace brazed in the same manner the laminate structure is bonded together, provided the areas outside the joint are protected against excessive heat.

Figure 15:
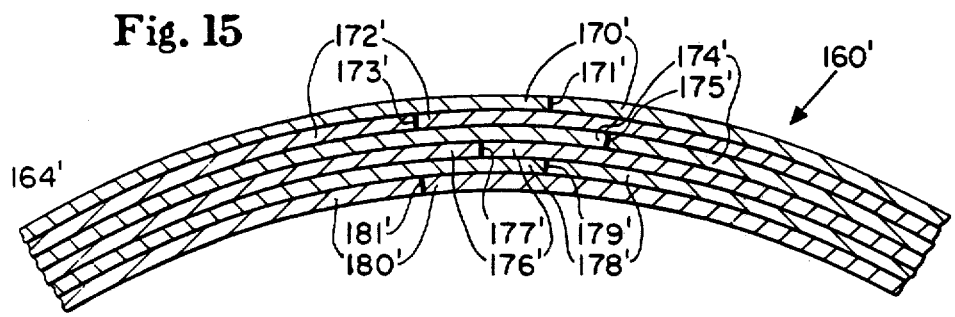
FIG. 15 is a view similar to that of FIG. 14 illustrating yet another lap seaming technique which can be used to join the free ends of the photoetched laminate structure to one another without substantially disrupting the three-dimensional pattern in the area of joinder.

FIG. 15 is a view similar to that of FIG. 14, but illustrating yet another lap seaming technique which may, if desired, be employed to join the free ends of laminar structures of the present invention to one another. Care must, however, be exercised with the construction generally illustrated in FIG. 15 to prevent non-adjacent lamina from bonding to one another at their free edges during the furnace brazing operation while the laminate structure is in planar condition. One method of avoiding such problems is to temporarily insert thin ceramic paper intermediate the non-adjacent lamina at the exposed edges during the planar phase of the furnace brazing operation.

In the tubular embodiment of FIG. 15, the free ends of tubular element 160' are interleaved with one another such that, if the slight differences in radius of curvature for each successive lamina in the stack are ignored, corresponding portions of the pattern contained in lamina 170' are mated to one another at 171'; corresponding portions of the pattern contained in lamina 172' are mated to one another at 173'; corresponding portions of the pattern contained in lamina 174' are mated to one another at 175'; corresponding portions of the pattern contained in lamina 176' are mated to one another at 177'; corresponding portions of the pattern contained in lamina 178' are mated to one another at 179'; and corresponding portions of the pattern contained in lamina 180' are mated to one another at 181'. Thus, no lamina seam is in radial alignment with an adjacent lamina seam, yet the three-dimensional pattern existing between the outermost surface 164' and the innermost surface 165' of the tubular member 160' is substantially continuous at any point along the periphery of the drum, including the area of joinder of the free ends.

Thus the present invention, in addition to providing planar forming surfaces exhibiting a three-dimensional pattern unobtainable by prior art machining or weaving methods, may, if desired, be utilized to provide a cylindrical forming surface exhibiting substantial continuity of pattern along its entire periphery. This permits continuous formation of a plastic web exhibiting the desired three-dimensional pattern without a seam discontinuity of the type typically present in prior art forming surfaces. As will be readily apparent to those skilled in the art, the present invention may be applied to great advantage to produce either perforate or imperforate plastic webs exhibiting nearly any three-dimensional pattern, characteristic, property or appearance desired. The webs may be made fluid-pervious in certain areas and fluid-impervious in others by controlling the level of differential pressure applied to the film during the debossing operation.

The inherent flexibility of photographic techniques makes it feasible to create nearly any structure desired by designing the particular characteristics sought into each layer and thereafter photographically reducing or enlarging the size of the pattern to whatever scale is desired in the photoetched lamina. In other embodiments of the present invention photographs of existing structures exhibiting desirable characteristics could be utilized to form one or more of the photoetched lamina. A composite stack of individual lamina may thereafter be assembled to produce a laminate forming surface exhibiting characteristics and properties not achievable by prior art machining and/or weaving means. For example, lamina of identical patterns and having identically sized apertures from one laminate to the next may be stacked to form straight-walled forming surfaces, lamina of similar patterns and having apertures of differing size may be stacked to form non-straight walled forming surfaces, lamina of dissimilar patterns may be stacked to form fine scale capillary networks which subdivide intermediate the uppermost and lowermost surfaces of the stack, etc.

Figure 16:
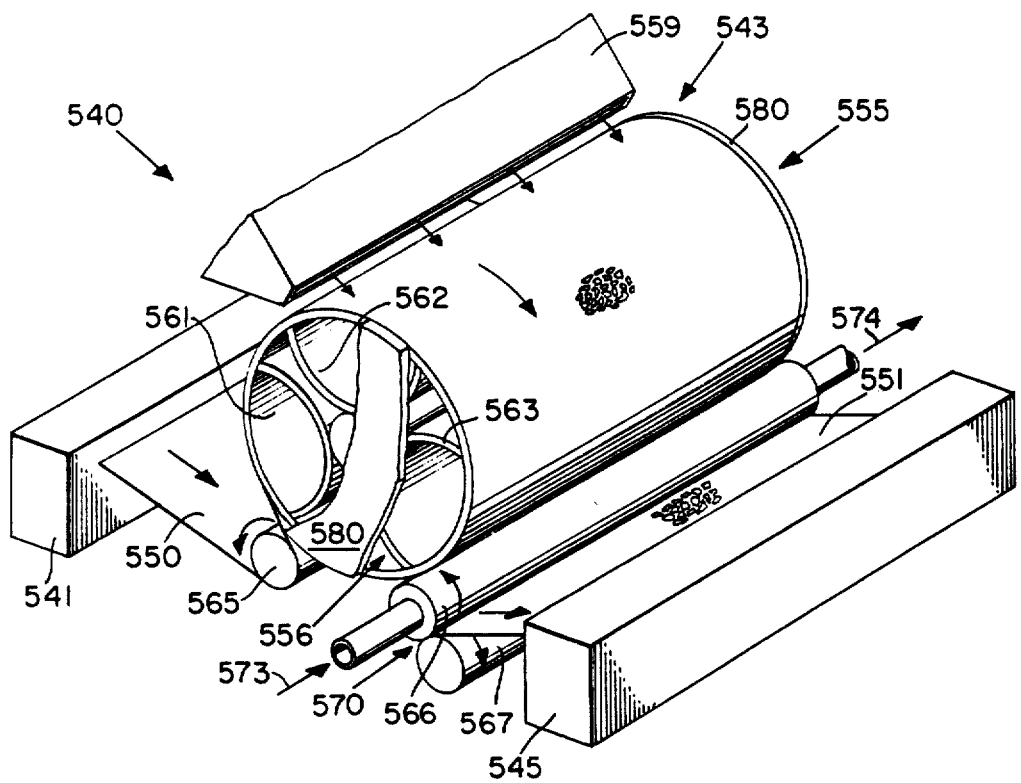
FIG. 16 is a simplified schematic illustration of a preferred method and apparatus for debossing and/or perforating a plastic film generally in accordance with the present invention.

A particularly preferred continuous film forming process which may employ a tubular laminate forming surface of the type generally shown in FIGS. 14 and 15 is schematically illustrated in FIG. 16. This process is generally described in the aforementioned patent application of Malcolm B. Lucas and Robert H. Van Coney entitled "METHOD OF AND APPARATUS FOR DEBOSSING AND PERFORATING A RUNNING RIBBON OF THERMOPLASTIC FILM⇌, Ser. No. 733,961, filed Oct. 19, 1976, issued as U.S. Pat. No. 4,151,240 on Apr. 24, 1979, and incorporated herein by reference. A particularly preferred apparatus 540 of the type disclosed in said patent application is schematically shown in FIG. 16. It includes constant tension film supply means 541, debossing and perforating means 543, and constant tension film forwarding and winding means 545. The frame, bearings, supports and the like which must necessarily be provided with respect to the functional members of apparatus 540 are not shown or described in detail in order to simplify and more clearly depict and disclose the present invention, it being understood that such details would be obvious to persons of ordinary skill in the art of designing plastic film converting machinery.

Briefly, apparatus 540, FIG. 16, comprises means for continuously converting a ribbon of thermoplastic film 550 into a debossed and perforated film 551 by directing hot air jets against one surface of the film while applying vacuum adjacent the opposite surface of the film, and while maintaining sufficient control of the film 550 to substantially obviate wrinkling and/or macroscopically distending the film. Thus, as will be more fully described hereinafter, apparatus 540 comprises means for maintaining constant machine direction tension in the film both upstream and downstream of a zone where the temperature is greater than the thermoplastic temperature of the film, but in which zone there is substantially zero machine direction and cross-machine direction tension tending to macroscopically distend the film. The tension is required to control and smooth a running ribbon of thermoplastic film; the zero tension zone results from the film in the zone being at a sufficiently high temperature to enable debossing and, if desired, perforating it through the use of heat and vacuum. FIG. 16 also shows greatly enlarged scale perforations in film 551 to enable visually perceiving the nature of the difference between the imperforate film 550 and the debossed and perforated film 551 as more fully described hereinafter.

As can be seen in FIG. 16, the debossing and perforating means 543 includes a rotatably mounted debossing-perforating cylinder 55 having closed ends 580, a nonrotating triplex vacuum manifold assembly 556 and hot air jet means 559. The triplex vacuum manifold assembly 556 comprises three manifolds designated 561, 562, and 563. Also shown in FIG. 16 is a freely rotatable lead-on idler roll 565, a power rotated lead-off/chill roll 566, and a soft-face (e.g., low density neoprene) roll 567 which is driven with the chill roll. Briefly, by providing means (not shown) for independently controlling the degree of vacuum in the three vacuum manifolds, a thermoplastic ribbon of film running circumferentially about a portion of the debossing-perforating cylinder 555 is sequentially subjected to a first level of vacuum by manifold 561, a second level of vacuum by manifold 562, and a third level of vacuum by manifold 563. As will be described more fully hereinafter, the vacuum applied to the film by manifold 561 enables maintaining upstream tension in the film, vacuum applied by manifold 562 enables perforating the film when hot air is directed radially inwardly against the film, and vacuum applied by manifold 563 enables cooling the film to below its thermoplastic temperature and enables establishing downstream tension therein. If desired, the film-contacting surface of the debossing-perforating cylinder 555 may be preheated prior to reaching vacuum manifold 562 by means well known in the art (and therefore not shown) to facilitate better conformance of plastic films comprised of flow-resistant polymers during the debossing operation. The nip 570 intermediate chill roll 566 and the soft-face roll 567 is only nominally loaded because high pressure would iron-out the three-dimensional debossments which are formed in the film in the aforementioned manner. However, even nominal pressure in nip 570 helps the vacuum applied by manifold 563 to isolate downstream tension (i.e., roll winding tension) from the debossing-perforating portion of the debossing-perforating cylinder 555, and enables the nip 570 to peel the debossed and perforated film from the debossing-perforating cylinder 555. Moreover, while vacuum drawn ambient air passing through the film into manifold 563 will normally cool the film to below its thermoplastic temperature, the passage of coolant through the chill roll as indicated by arrows 573, 574 in FIG. 16 will enable the apparatus to handle thicker films or be operated at higher speeds.

To summarize, the first vacuum manifold 561, and the third vacuum manifold 563 located within the debossing-perforating cylinder 555 enable maintaining substantially constant upstream and downstream tension respectively in a running ribbon of film while the intermediate portion of the film adjacent the second vacuum manifold 562 within the debossing-perforating cylinder 555 is subjected to tension vitiating heat and vacuum to effect debossing and perforating of the film.

Referring again to FIG. 16, the constant tension film supply means 541 and the constant tension film forwarding and winding means 545 may, if desired, be substantially identical to and function substantially identically to the corresponding portions of the apparatus shown and described in U.S. Pat. No. 3,674,221 issued to Riemersma on July 4, 1972 and which is hereby incorporated herein by reference. The debossing and perforating means 543 comprises the rotatably mounted debossing-perforating cylinder 555, means (not shown) for rotating the cylinder 555 at a controlled peripheral velocity, the non-rotating triplex vacuum manifold assembly 556 inside the debossing-perforating cylinder 555, means (not shown) for applying controlled levels of vacuum inside the three vacuum manifolds 561, 562 and 563 comprising the triplex manifold assembly 556, and hot air jet means 559.

The debossing-perforating cylinder 555 may be constructed by generally following the teachings of the aforementioned commonly assigned, patent application of Malcolm B. Lucas and Robert H. Van Coney, but substituting a tubular laminate forming surface of the present invention for the perforated tubular forming surface disclosed therein.

While a preferred application of the disclosed photo-etched laminate structure is in a vacuum film forming operation as generally outlined in the aforementioned patent application of Malcolm B. Lucas et al., it is anticipated that photoetched laminate forming structures of the present invention could be employed with equal facility to directly form a three-dimensional plastic structure of the present invention. Such a procedure would involve applying a heated fluid plastic material, typically a thermoplastic resin, directly to the forming surface, applying a sufficiently great pneumatic differential pressure to the heated fluid plastic material to cause said material to conform to the image of the perforate laminate forming surface, allowing the fluid material to solidify, and thereafter removing the three-dimensional plastic structure from the forming surface. It is further anticipated that the present technology could, if desired, be incorporated in suitably reinforced film embossing rolls and the like, provided only that the embossing pressures to which the rolls will ultimately be subject are not so great as to destroy the particular three-dimensional pattern exhibited by the laminate embossing surface. A resilient back-up roll could, if desired, be utilized in such an embossing operation to avoid damaging the laminate embossing surface. It is even further anticipated that laminate forming surfaces of the present invention may find utility in applications other than plastic film forming.

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A resilient three-dimensional web exhibiting a fiber-like appearance and tactile impression and comprised of fluid-impervious plastic material, said web having first and second surfaces, said first surface having a multiplicity of apertures therein, each of said apertures being defined by a multiplicity of intersecting fiber-like elements interconnected to one another in the plane of said first surface, each of said fiber-like elements further exhibiting a substantially uniform U-shaped cross-section along its length, said cross-section comprising a base portion in said plane of said first surface and a sidewall portion joined to each edge of said base portion, said sidewall portions extending generally in the direction of said second surface of said web, said intersecting sidewall portions being interconnected to one another intermediate said first and said second surfaces of said web, said interconnected sidewall portions terminating substantially concurrently with one another in the plane of said second surface.

2. The resilient three-dimensional web of claim 1, wherein said second surface of said web contains a multiplicity of apertures and said interconnected sidewall portions of said fiber-like elements terminate substantially concurrently with one another in said apertures in the plane of said second surface.

3. The resilient three-dimensional web of claim 2, wherein said apertures in said second surface of said web are defined by said interconnected sidewall portions of said fiber-like elements terminating substantially concurrently with one another in the plane of said second surface.

4. The resilient three-dimensional web of claim 2, wherein said interconnected sidewall portions form a discrete capillary network connecting each of said apertures formed by said multiplicity of intersecting fiber-like elements in said first surface of said web exclusively with a corresponding aperture defined by said interconnected sidewall portions in said second surface of said web.

5. The resilient three-dimensional web of claim 2, wherein at least a portion of said fiber-like elements are substantially straight along a portion of their length.

6. The resilient three-dimensional web of claim 5, wherein at least a portion of said fiber-like elements are substantially straight along their entire length.

7. The resilient three-dimensional web of claim 2, wherein said sidewall portions of said fiber-like elements are oriented substantially perpendicular to the base portions of said fiber-like elements.

8. The resilient three-dimensional web of claim 4, wherein said capillary networks are of non-uniform cross-section along their length.

9. The resilient three-dimensional web of claim 4, wherein said capillary networks connecting said apertures in said first surface of said web exclusively with the corresponding apertures in said second surface of said web are of decreasing cross-section in the direction of said second surface, thereby promoting rapid transmission of fluids deposited on said apertures in said first surface to the corresponding apertures in said second surface without lateral transmission of said fluids between adjacent capillary networks.

10. The resilient three-dimensional web of claim 2, wherein said fluid-impervious plastic material comprises a thermoplastic film.

11. The resilient three-dimensional web of claim 2, wherein said first surface of said web exhibits a fine scale surface roughness comprising a pattern of ridges and valleys to minimize gloss.

12. The resilient three-dimensional web of claim 9, wherein said ridges and valleys are aligned substantially parallel to one another.

13. A resilient three-dimensional web exhibiting a fiber-like appearance and tactile impression and comprised of fluid-impervious plastic material, said web having first and second surfaces, said first surface having a multiplicity of apertures therein, each of said apertures being defined by a multiplicity of intersecting primary fiber-like elements interconnected to one another in the plane of said first surface, each of said primary fiber-like elements exhibiting a substantially uniform U-shaped cross-section along its length, said cross-section comprising a primary base portion in said plane of said first surface and a primary sidewall portion joined to each edge of said primary base portion, said primary sidewall portions extending generally in the direction of said second surface of said web, said intersecting primary sidewall portions being interconnected to one another intermediate said first and said second surfaces of said web, said interconnected primary sidewall portions being further connected to at least one intersecting secondary fiber-like element exhibiting a substantially uniform U-shaped cross-section along its length, said cross-section of said secondary element comprising a secondary base portion located in a plane intermediate said first and second surfaces of said web and a secondary sidewall portion joined to each edge of said secondary base portion, said secondary sidewall portions also extending generally in the direction of said second surface of said web, said secondary sidewall portions being interconnected to said intersecting primary sidewall portions intermediate the plane of said secondary base portion and the plane of said second surface of said web, said interconnected primary and secondary sidewall portions terminating substantially concurrently with one another in the plane of said second surface.

14. The resilient three-dimensional web of claim 13, wherein said second surface of said web contains a multiplicity of apertures and said interconnected primary and secondary sidewall portions of said fiber-like elements terminate substantially concurrently with one another in said apertures in the plane of said second surface.

15. The resilient three-dimensional web of claim 14, wherein said apertures in said second surface of said web are defined by said interconnected primary and secondary sidewall portions of said fiber-like elements located intermediate said first and said second surfaces of said web, said interconnected primary and secondary sidewall portions thereby forming a discrete capillary network connecting each of said apertures defined by said multiplicity of intersecting primary fiber-like elements in the plane of said first surface of said web exclusively with a multiplicity of said apertures formed in said second surface of said web by said interconnected primary and secondary sidewall portions of said fiber-like elements.

16. The resilient three-dimensional web of claim 14, wherein at least a portion of said primary fiber-like elements are substantially straight along a portion of their length.

17. The resilient three-dimensional web of claim 16, wherein at least a portion of said secondary fiber-like elements are substantially straight along a portion of their length.

18. The resilient three-dimensional web of claim 15, wherein said capillary networks are of non-uniform cross-section along their length.

19. The resilient three-dimensional web of claim 18, wherein said capillary networks connecting each of said apertures in said first surface of said web exclusively with the corresponding multiplicity of apertures in said second surface of said web are of decreasing cross-section in the direction of said second surface, thereby promoting rapid transmission of fluids deposited on each of said apertures in said first surface to the corresponding multiplicity of apertures in said second surface without lateral transmission of said fluids between adjacent capillary networks.

20. The resilient three-dimensional web of claim 14, wherein said fluid-impervious plastic material comprises a thermoplastic film.

21. The resilient three-dimensional web of claim 14, wherein said first surface of said web exhibits a fine scale surface roughness comprising a pattern of ridges and valleys.

22. The resilient three-dimensional web of claim 21, wherein said ridges and valleys are aligned substantially parallel to one another.

23. The resilient three-dimensional web of claim 13, wherein said interconnected primary and secondary sidewall portions are further connected to at least one intersecting tertiary fiber-like element exhibiting a substantially uniform U-shaped cross-section along its length, said cross-section of said tertiary element comprising a tertiary base portion located in a plane intermediate said plane of said secondary base portion and said plane of said second surface, said tertiary fiber-like element further including a tertiary sidewall portion joined to each edge of said tertiary base portion, said tertiary sidewall portions also extending generally in the direction of said second surface of said web, said tertiary sidewall portions being interconnected to said intersecting primary and secondary sidewall portions intermediate the plane of said tertiary base portion and the plane of said second surface, said intersecting primary, secondary and tertiary sidewall portions terminating substantially concurrently with one another in the plane of said second surface.

24. The resilient three-dimensional web of claim 23, wherein said second surface of said web contains a multiplicity of apertures and said interconnected primary, secondary and tertiary sidewall portions of said fiber-like elements terminate substantially concurrently with one another in said apertures in the plane of said second surface.

25. The resilient three-dimensional web of claim 24, wherein said apertures in said second surface of said web are defined by said interconnected primary, secondary and tertiary sidewall portions of said fiber-like elements located intermediate said first and said second surfaces of said web, said interconnected primary, secondary and tertiary sidewall portions thereby forming a discrete capillary network connecting each of said apertures defined by said multiplicity of intersecting primary fiber-like elements in the plane of said first surface of said web exclusively with a multiplicity of said apertures formed in said second surface of said web by said interconnected primary, secondary and tertiary sidewall portions of said fiber-like elements.

26. The resilient three-dimensional web of claim 25, wherein said capillary networks are of non-uniform cross-section along their length.

27. The resilient three-dimensional web of claim 26, wherein said capillary networks connecting each of said apertures in said first surface of said web exclusively with the corresponding multiplicity of apertures in said second surface of said web are of decreasing cross-section in the direction of said second surface, thereby promoting rapid transmission of fluids deposited on each of said apertures in said first surface to the corresponding multiplicity of apertures in said second surface without lateral transmission of said fluids between adjacent capillary networks.

28. The resilient three-dimensional web of claim 24, wherein said fluid-impervious plastic material comprises a thermoplastic film.

29. The resilient three-dimensional web of claim 24, wherein said first surface of said web exhibits a fine scale surface roughness comprising a pattern of ridges and valleys.

30. The resilient three-dimensional web of claim 29, wherein said ridges and valleys are aligned substantially parallel to one another.

31. An absorbent bandage comprising a wearer-contacting topsheet and an absorbent element for absorbing body fluids, said topsheet comprising a resilient three-dimensional web having a first surface for contacting the wearer and a second surface having a multiplicity of apertures therein contacting said absorbent element, said web being comprised of fluid-impervious plastic material, said web exhibiting a fiber-like appearance and tactile impression, said first surface of said web also having a multiplicity of apertures therein, each of said apertures being defined by a multiplicity of intersecting fiber-like elements interconnected to one another in the plane of said first surface, each of said fiber-like elements further exhibiting a substantially uniform U-shaped cross-section along its length, said cross-section comprising a base portion in said plane of said first surface and a sidewall portion joined to each edge of said base portion, said sidewall portions extending generally in the direction of said second surface of said web, said intersecting sidewall portions being interconnected to one another intermediate said first and said second surfaces of said web, said interconnected sidewall portions terminating substantially concurrently with one another in said apertures in the plane of said second surface.

32. The absorbent bandage of claim 31, including a backsheet resistant to the passage of aqueous fluid therethrough secured in superposed relation to said bandage adjacent the surface of said absorbent element opposite said topsheet.

33. The structure of claim 31, wherein said absorbent bandage comprises a disposable diaper.

34. The structure of claim 31, wherein said absorbent bandage comprises a disposable catamenial appliance.

35. An absorbent bandage comprising a wearer-contacting topsheet and an absorbent element for absorbing body fluids, said topsheet comprising a resilient three-dimensional web having a first surface for contacting the wearer and a second surface having a multiplicity of apertures therein contacting said absorbent element, said web being comprised of fluid-impervious plastic material, said web exhibiting a fiber-like appearance and tactile impression, said first surface of said web also having a multiplicity of apertures therein, each of said apertures being defined by a multiplicity of intersecting primary fiber-like elements interconnected to one another in the plane of said first surface, each of said primary fiber-like elements exhibiting a substantially uniform U-shaped cross-section along its length, said cross-section comprising a primary base portion in said plane of said first surface and a primary sidewall portion joined to each edge of said primary base portion, said primary side-wall portions extending generally in the direction of said second surface of said web, said intersecting primary sidewall portions being interconnected to one another intermediate said first and said second surfaces of said web, said interconnected primary sidewall portions being further connected to at least one intersecting secondary fiber-like element exhibiting a substantially uniform U-shaped cross-section along its length, said cross-section of said secondary element comprising a secondary base portion located in a plane intermediate said first and second surfaces of said web and a secondary sidewall portion joined to each edge of said secondary base portion, said secondary sidewall portions also extending generally in the direction of said second surface of said web, said secondary sidewall portions being interconnected to said intersecting primary sidewall portions intermediate the plane of said secondary base portion and the plane of said second surface of said web, said interconnected primary and secondary sidewall portions terminating substantially concurrently with one another in said apertures in the plane of said second surface.

36. An absorbent bandage comprising an absorbent element for absorbing body fluids and a breatheable backsheet resistant to aqueous fluid passage secured adjacent said absorbent element opposite the wearer contacting surface of said absorbent element, said backsheet comprising a resilient three-dimensional web having a first surface opposite the wearer-contacting surface of said absorbent bandage and a second surface having a multiplicity of apertures therein contacting said absorbent element, said web being comprised of fluid-impervious plastic material, said web exhibiting a fiber-like appearance and tactile impression, said first surface of said web having a multiplicity of apertures therein, each of said apertures being defined by a multiplicity of intersecting fiber-like elements interconnected to one another in the plane of said first surface, each of said fiber-like elements exhibiting a substantially uniform U-shaped cross-section along its length, said cross-section comprising a base portion in said plane of said first surface and a sidewall portion joined to each edge of said base portion, said sidewall portions extending generally in the direction of said second surface of said web, said intersecting sidewall portions being interconnected to one another intermediate said first and said second surfaces of said web, said interconnected sidewall portions thereby forming a discrete capillary network connecting each of said apertures defined by multiplicity of intersecting fiber-like elements in the plane of said first surface of said web exclusively with an aperture formed in said second surface of said web by said interconnected sidewall portions of said fiber-like elements, said capillary network being of decreasing cross-section in the direction of said second surface, whereby said capillary network resists aqueous fluid transport from said second surface to said first surface while permitting vapors to pass readily through said backsheet.

37. The absorbent bandage of claim 36, including a fluid-pervious topsheet secured in superposed relation to said bandage adjacent the surface of said absorbent element opposite said backsheet.

* * * * *

UNITED STATES PATENT AND TRADEMARK OFFICE
CERTIFICATE OF CORRECTION

PATENT NO. : 4,342,314
DATED : August 3, 1982
INVENTOR(S) : CLIFFORD J. RADEL and HUGH A THOMPSON It is certified that error appears in the above-identified patent and that said Letters Patent are hereby corrected as shown below:

Column 2, line 41, "peripery" should read -- periphery --.

Column 5, line 6, "breathable" should read -- breatheable --.

Column 7, line 57, "diaposable" should read -- disposable --.

Column 9, line 58, "adsorbent" should read -- absorbent --.

Column 11, line 51, "directon" should read -- direction --.

Column 13, line 9, delete "of" second occurrence.

Column 14, line 54, "breathability" should read -- breatheability --.

Column 18, line 4, "borader" should read -- border --.

Column 18, line 13, "in" should read -- is --.

Column 22, line 49, "stucture" should read -- structure --.

Column 25, line 15, " ⇌ ," should read -- ", --.

Signed and Sealed this

Sixteenth Day of November 1982

[SEAL]

Attest:

GERALD J MOSSINGHOFF

*Attesting Officer*     *Commissioner of Patents and Trademarks*